(12) United States Patent
Meuillet et al.

(10) Patent No.: US 10,179,142 B2
(45) Date of Patent: Jan. 15, 2019

(54) TREATMENT AND/OR PREVENTION OF BONE METASTASIS

(71) Applicants: The Arizona Board of Regents on behalf of The University of Arizona, Tucson, AZ (US); Board of Regents, The University of Texas System, Austin, TX (US)

(72) Inventors: Emmanuelle Meuillet, Tucson, AZ (US); Sylvestor Moses, Tucson, AZ (US); Shuxing Zhang, Houston, TX (US)

(73) Assignee: THE ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 14/916,904

(22) PCT Filed: Sep. 4, 2014

(86) PCT No.: PCT/US2014/054129
§ 371 (c)(1),
(2) Date: Mar. 4, 2016

(87) PCT Pub. No.: WO2015/035072
PCT Pub. Date: Mar. 12, 2015

(65) Prior Publication Data
US 2016/0213693 A1 Jul. 28, 2016

Related U.S. Application Data

(60) Provisional application No. 61/873,731, filed on Sep. 4, 2013.

(51) Int. Cl.
| | | |
|---|---|---|
| *A61K 31/519* | (2006.01) | |
| *A61K 31/4164* | (2006.01) | |
| *A61K 31/4196* | (2006.01) | |
| *A61K 31/42* | (2006.01) | |
| *A61K 31/635* | (2006.01) | |
| *A61K 31/433* | (2006.01) | |
| *A61K 31/496* | (2006.01) | |
| *A61K 31/63* | (2006.01) | |
| *A61K 31/4439* | (2006.01) | |
| *G01N 33/574* | (2006.01) | |

(52) U.S. Cl.
CPC ........ *A61K 31/635* (2013.01); *A61K 31/4196* (2013.01); *A61K 31/433* (2013.01); *A61K 31/4439* (2013.01); *A61K 31/496* (2013.01); *A61K 31/519* (2013.01); *A61K 31/63* (2013.01); *G01N 33/57434* (2013.01); *A61K 31/4164* (2013.01); *A61K 31/42* (2013.01); *G01N 2333/47* (2013.01)

(58) Field of Classification Search
CPC .............. A61K 31/365; A61K 31/4195; A61K 31/519; A61K 31/4164; A61K 31/4196; A61K 31/42
USPC .................... 514/158, 259.31, 364, 383, 385
See application file for complete search history.

(56) References Cited

FOREIGN PATENT DOCUMENTS

| WO | WO-2009/129267 A2 | 10/2009 |
|---|---|---|
| WO | WO-2011/032169 A2 | 3/2011 |
| WO | WO-2012/018982 A2 | 2/2012 |
| WO | WO-2013/178782 A1 | 12/2013 |

OTHER PUBLICATIONS

Meuillet et al., "Targeting the PH domain of TIAM1 to inhibit prostate cancer metastasis", Cancer Research, vol. 73, No. 8 Supplement., Abstract No. 5563 (Apr. 2013).*
Ward, et al., "The Long-Term Clinical Impact of Biochemical Recurrence of Prostate Cancer 5 or More Years After Radical Prostatectomy", The Journal of Urology, vol. 170, Nov. 2003, pp. 1872-1876.
Armstrong, et al., "Prediction of Survival Following First-Line Chemotherapy in Men with Castration-Resistant Metastatic Prostate Cancer", American Association for Cancer, www.aacrjournals.org, Dec. 15, 2009, pp. 203-212.
Debes, M.D., et al., "Mechanisms of Androgen-Refractory Prostate Cancer", The New England Journal of Medicine, Oct. 7, 2004, pp. 1488-1490.
Freedland, MD, et al., "Risk of Prostate Cancer-Specific Mortality Following Biochemical Recurrence After Radical Prostatectomy", American Medical Associate, vol. 294, No. 4, Jul. 27, 2005, pp. 433-439.
Mundy, "Metastasis to Bone: Causes, Consequences and Therapeutic Opportunities", Nature Publishing Group, Aug. 2002, vol. 2, pp. 584-593.
Hatoum, et al., "Zoledronic Acid Therapy Impacts Risk and Frequency of Skeletal Complications and Follow-up Duration in Prostate Cancer Patients with Bone Metastasis", Current Medical Research and Opinion, vol. 27, No. 1, Jan. 2011, pp. 55-62.

(Continued)

*Primary Examiner* — Kevin E Weddington
(74) *Attorney, Agent, or Firm* — Blank Rome LLP

(57) ABSTRACT

T-lymphocyte invasion and metastases (Tiam-1) has been identified as a marker and anti-cancer drug target for therapy of metastatic bone cancer in individuals afflicted with prostate cancer. The present disclosure provides methods and compounds for inhibiting metastases by disrupting Tiam-1 expression and activity. One particularly preferred compound comprises a disulfomanide of the formula.

10 Claims, 9 Drawing Sheets
Specification includes a Sequence Listing.

(56) References Cited

OTHER PUBLICATIONS

Saad, et al., "Role of Bisphosphonates in Prostate Cancer", European Urology, vol. 45, 2004, pp. 26-34.
Yu, et al., "Phase II Study of Dasatinib in Patients with Metastatic Castration-Resistant Prostate Cancer", Clinical Cancer Research, American Association for Cancer Research, vol. 15, No. 23, Dec. 1, 2009, pp. 7421-7429.
Li., et al., "PTEN, a Putative Protein Tyrosine Phosphatase Gene Mutated in Human Brain, Breast, and Prostate Cancer", Science, www.sciencemag.org, vol. 275, Mar. 28, 1997, pp. 1942-1947.
Suzuki et al., "Interfocal Heterogeneity of PTEN/MMAC1 Gene Alterations in Multiple Metastatic Prostate Cancer Tissues" Advances in Brief, Cancer Research, vol. 56, Jan. 15, 1998, pp. 204-209.
Yoshimoto, et al., "FISH Analysis of 107 Prostate Cancers Shows that PTEN Genomic Deletion is Associated with Poor Clinical Outcome", British Journal of Cancer, vol. 97, Aug. 14, 2007, pp. 678-685.
Carracedo, et al., "The PTEN-P13K Pathway: of Feedbacks and Cross-Talks", Oncogene, vol. 27, 2008, pp. 5527-5541.
Liliental et al., "Genetic Deletion of the Pten Tumor Suppresor Gene Promotes Cell Motility by Activation of Rac1 and Cdc42 GTPases", Current Biology, vol. 10, No. 7, Mar. 24, 2000, pp. 401-404.
Vivanco et al., "Identification of the JNK Signaling Pathway as a Functional Target of the Tumor Suppressor PTEN", Cancer Cell, vol. 11, Jun. 2007, pp. 555-569.
Minard et al., "The Role of the Guanine Nucleotide Exchange Factor Tiam1 in Cellular Migration, Invasion, Adhesion and Tumor Progression", Breast Cancer Research and Treatment, vol. 84, pp. 21-32.
Connolly, et al., "Tiam1-IRSp53 Complex Formation Directs Specificity of Rac-Mediated Actin Cytoskeleton Regulation", Molecular and Cellular Biology, vol. 25, No. 11, Jun. 2005, pp. 4602-4614.
Klooster et al., "Interaction Between Tiam1 and the Arp2/3 Complex Links Activation of Rac to Actin Polymerization", Biochemical Society, vol. 397, 2006, pp. 39-45.
Yamauchi et al., "Ras Activation of a Rac1 Exchange Factor, Tiam 1, Mediates Neurotrophin-3-Induced Schwann Cell Migration", PNAS, www.pnas.org/cgi/doi/10.1073/pnas.0507125102, vol. 102, No. 41, Oct. 11, 2005, pp. 14889-14894.
Engers, et al., "Prognostic Relevance of Tiam1 Protein Expression in Prostate Carcinomas", British Journal of Cancer, vol. 95, No. 8, 2006, pp. 1081-1086.
Strumane, et al., "The Rac Activator Tiam1 and Ras-Induced Oncogenesis", Methods in Enzymology, vol. 407, 2006, pp. 269-281.
Morinaga, et al., "Isolation of a Brefeldin A-Inhibited Guanine Nucleotide-Exchange Protein for ADP Ribosylation Factor (ARF) 1 and ARF3 that Contains a Sec7-Like Domain", Proc. Natl. Acad. Sci., vol. 93, Nov. 1996, pp. 12856-12860.
Schmidt, et al., "Identification of the First Rho-GEF Inhibitor; TRIPα, which Targets the RhoA-specific GEF Domain of Trio", Federation of European Biochemical Societies, FEBS Letters, vol. 523, 2002, pp. 35-42.
Gao, et al., "Rational Design and Characterization of a Rac GTPase-Specific Small Molecule Inhibitor", PNAS, www.pnas.org/cgi/doi/10.1073/pnas.0307512101; May 18, 2004, vol. 101, No. 20, pp. 7618-7623.
Taylor, et al., "Integrative Genomic Profiling of Human Prostate Cancer", Cancer Cell, vol. 18, Jul. 13, 2010, pp. 11-22.
Cerami, et al., "The c-Bio Cancer Genomics Portal: An Open Platform for Exploring Multidimensional Cancer Genomics Data", American Association for Cancer Research, www.aacrjournals.org, May 2012, 6 pages.
Worthylake, et al., "Crystal Structure of Rac1 in Complex with the Guanine Nucleotide Exchange Region of Tiam1", Nature, www.nature.com, vol. 408, Dec. 7, 2000, pp. 682-688.

Baumeister, et al., "Loss of Phosphatidylinositol 3-Phospiate Binding by the C-Terminal Tiam-1 Pleckstrin Homology Domain Prevents in Vivo Rac1 Activation without Affecting Membrane Targeting", The Journal of Biological Chemistry, vol. 278, No. 13, Mar. 28, 2003, pp. 11457-11464.
Zhang, et al., "Development and Evaluation of a New Statistical Model for Structure-Based High-Throughput Virtual Screening", Int. J. Bioinformatics Research and Applications, vol. 5, No. 3, 2009, pp. 269-279.
Zhang, et al., "DOVIS: An Implementation for High-Throughput Virtual Screening Using AutoDock", BMC Bioinformatics, Feb. 27, 2008; vol. 9, No. 126; 4 pages.
Moses, et al., "In vitro and In vivo Activity of Novel Small Molecule Inhibitors Targeting the Pleckstrin Homology Domain of Protein Kinase B/AKT", American Association for Cancer Research, www.aacrjournals.org, Jun. 15, 2009, vol. 69, No. 12, 11 pages.
Ahad, et al., "Development of Sulfonamide AKT PH Domain Inhibitors", Bioorganic & Medicinal Chemistry, vol. 19, 2011, pp. 2046-2054.
Stea, et al., Time and Dose-Dependent Radiosensitization of the Glioblastoma Multiforme U251 Cells by the EGF Receptor Tyrosine Kinase Inhibitor ZD1839 ('Iressa'), Science Direct, Cancer Letters, vol. 202, 2003, pp. 43-51.
Paine-Murrieta, et al., "Human Tumor Models in the Severe combined Immune Deficient (scid) Mouse", Cancer Chemother Pharmacol, vol. 40, 1997, pp. 209-214.
Adams, et al., "Regulation of Breast Cancer Cell Motility by T-Cell Lymphoma Invasion and Metastasis-Inducing Protein", Breast Cancer Research, vol. 12, 2010, pp. 1-15.
Lane, et al., "The Expression and Prognostic Value of the Guanine Nucleotide Exchange Factors (GEFs) Trio, Vavl and TIAM-1 in Human Breast Cancer", International Seminars in Surgical Oncology, Oct. 16, 2008, vol. 5, No. 23, pp. 1-7.
Lesson et al., "The Influence of Drug-Like Concepts on Decision-Making in Medicinal Chemistry", Nature REviews, Drug Discovery, Nov. 2007, vol. 6, pp. 881-890.
Habets, et al., "Identification of an Invasion-Inducing Gene, Tiam-1, That Encodes a Protein with Homology to GDP-GTP Exchangers for Rho-Like Proteins", Cell, vol. 77, May 20, 1994, pp. 537-549.
Alexander, et al., "N-cadherin Gene Expression in Prostate Carcinoma is Modulated by Integrin-Dependent Nuclear Translocation of Twist1", American Association for Cancer Research, www.aacrjournals.org, vol. 66, No. 7, Apr. 1, 2006, 6 pages.
Minard, et al., "Tiam1 Regulates Cell Adhesion, Migration and Apoptosis in Colon Tumor Cells", Clin. Exp. Metastasis, vol. 23, 2006, pp. 301-313.
Singh, et al., "In Vivo Models of Prostate Cancer Metastasis to Bone", The Journal of Urology, vol. 174, Sep. 2005, pp. 820-826.
Saad, "Role of Bisphosphonates in Non-Metastatic Prostate Cancer", www.thelancet.com/oncology, vol. 15, Sep. 2014, 2 pages.
Berge, et al., "Pharmaceutical Salts", Journal of Pharmaceutical Sciences, vol. 66, No. 1, Jan. 1977, pp. 1-19.
Bundgard, "Design of Prodrugs", Science-Engineering Library IN, 1985, pp. 7-9 and 21-24.
Prescott, "Methods in Cell Biology", Science-Engineering Library, vol. 14, No. 33, 1976, 2 pages.
Wu, et al., "First-Pass Metabolism via UDP-Glucuronosyltransferase: a Barrier to Oral Bioavailability of Phenolics", Journal of Pharmaceutical Sciences, vol. 100, No. 9, Sep. 2011, pp. 3655-3681.
Du-Cuny et al., "Computational Modeling of Novel Inhibitors Targeting the Akt Pleckstrin Homology Domain", Bioorganic & Medicinal Chemistry, vol. 17, No. 19, Oct. 1, 2009, pp. 6983-6992.
He Jin et al., "Methylation Status of T-Lymphoma Invasion and Metastasis 1 Promoter and Its Overexpression in Colorectal Cancer", Human Pathology, vol. 42, No. 4, Aug. 25, 2010, pp. 541-551.
Liu et al., "Expression of Tiam1 Predicts Lymph Node Metastasis and Poor Survival of Lung Adenocarcinoma Patients", Diagnostic Pathology, BioMed Central Ltd., vol. 9, No. 1, Mar. 24, 2014, p. 69.

* cited by examiner

SEQUENCE LISTING

<160> NUMBER OF SEQ ID NOS: 2

<210> SEQ ID NO 1
<211> LENGTH: 58
<212> TYPE: DNA
<213> ORGANISM: Homo sapiens

<400> SEQUENCE: 1
ccgggttggt cgaattgtct tagaactcga gttctaagac aattcgacca acttttg        58

<210> SEQ ID NO 2
<211> LENGTH: 58
<212> TYPE: DNA
<213> ORGANISM: Homo sapiens

<400> SEQUENCE: 2
ccggcctgag gatgcggata tagatctcga gatctatatc cgcatcctca ggttttg        58

TREATMENT AND/OR PREVENTION OF BONE METASTASIS

The present disclosure is directed to methods and compositions for inhibiting metastases in mammals stricken with cancer. The disclosure has particular utility in connection with the inhibition of bone metastases in individuals afflicted with prostate cancer and will be described in connection with such utility, although other utilities are contemplated.

Metastasis, the process whereby tumor cells migrate throughout the body, is complex. In order for a tumor to produce metastases it must contain cells of the correct genotype be capable of completing a complex series of steps. The steps of tumor cell metastasis include the detachment of tumor cells from the primary neoplasm, invasion into the surrounding stroma, intravasation into the vasculature of lymphatic system, survival in the circulation, extravasation into the new host organ or tissue, and then survival and growth in this new microenvironment. Specific genes are likely to control specific events at each of these steps; however, to date, relatively few genes have been implicated in the process of tumor metastasis.

Prostate Cancer (PCA) is a heterogeneous disease and the 5-year survival rate for men whose cancer has metastasized at the time of diagnosis is about 27.8%. However, if the cancer is detected prior to metastasis the 5-year survival rate increases to nearly 100% [1] Currently, it is not possible to predict at the time of biopsy which tumors are significant and will prove fatal through metastatic dissemination versus those that will remain organ confined for many years [2, 3] It is estimated that about 20-30% of men in the U.S. develop biochemical recurrent cancer following prostatectomy [4] and androgen-deprivation therapy (ADT) the mainstay for systemic treatment of newly diagnosed PCA. Although most patients respond to androgen suppression by entering into clinical remission, they often develop more aggressive tumors that are castration-resistant metastatic PCA (CR-PCA). PCA metastases to the bone are the major cause of patient mortality [5]. Different therapeutic strategies have been developed to inhibit the primary and metastatic cancer cell as well as the bone microenvironment including biphosphonates and more recently Src family kinase inhibitors [6-8]. However, there is a major unmet need to develop targeted drugs for CRPCA skeletal metastases.

PTEN loss is a common molecular event in PCA and CRPCA. The inactivation of the tumor suppressor PTEN is the most frequent genetic alteration in this disease, and it has a critical role in prostate oncogenesis, biochemical recurrence, and development of androgen independence. Deletion or mutation of one PTEN allele occurs in 20-40% of localized cancers and 60% of metastases [9-11]. Loss of PTEN results in Phosphatidyl-Inositol-3-Kinase (PI3K) activation of downstream pathways, such as Akt, Rac1-Guanine Exchange Factors (GEFs) and p21-activated kinases (PAK), and the JNK pathways [12-14]. Deregulated PI3K signaling activates Rac1 through Rac-GEFs. PTEN$^{-/-}$ MEFs were found to have increased cell migration with a significant increase in Rac1 activity underlying an important role of GEFs [15].

T-lymphocyte invasion and metastasis (Tiam-1) is a Rac1-GEF that is involved in cell polarity, adhesion, migration, and invasion [15]. The structure of Tiam-1 is conserved between vertebrates and the protein contains a variety of structural motifs: a myristoylated N-terminus, 2 N-terminal PEST domains, an N-terminal pleckstrin homology domain (nPH), a coiled-coil region with adjacent sequence (CC-Ex), a Ras-binding domain (RBD), a PSD-95/DlgA/ZO-1 domain (PDZ) and a catalytic Dbl homology (DH)/C-terminal PH domain (cPH). Tiam-1 is specific to the GTPase Rac1, whereby it can activate p21-activating kinase (PAK1). Tiam-1 also indirectly coordinates interactions with the WAVE2 scaffold [16] and interacts with the p21-Arc subunit of the Arp2/3 complex leading to cell motility and morphological changes via actin cytoskeleton rearrangements [17]. Lastly, activation of Rac1 and the JNK pathway by Tiam-1 has been shown to promote migration in nuerotrophin-3 induced Schwann cells [18]. Tiam-1 has been shown to be over-expressed in PCA where it is an independent predictor of decreased disease free survival [19]. Finally, over-expression of Tiam-1 is associated with increased metastatic potential in PCA cell lines [15, 20]. More recently, Tiam-1 was suggested as a potential therapeutic target for the treatment of metastatic diseases. Currently, the only known inhibitors for GEFs are Brefeldin A [21], various RNA aptamers [22] and peptides, as well as NSC23766 (a weak non-specific Tiam-1/Rac1 inhibitor) [23]. However, these compounds are limited by either high cytotoxicity or poor cell permeability, which renders them unsuitable for clinical use. Hence, there is a clear need to develop compounds targeting Tiam-1 in order to impede tumor invasion and metastasis.

We have identified Tiam-1 as a useful biomarker and anti-cancer drug target for therapy of metastatic prostate cancer in individuals afflicted with advanced prostate cancer (PCa). The present disclosure in one aspect provides methods and compounds for inhibiting metastases by disruption of Tiam-1 activity.

More particularly, the present disclosure is based in part on the identification of certain compounds set forth below, which advantageously impede tumor invasion and metastasis in mammals by inhibiting the activation of Rac1 via targeting the GEF function of the Tiam-1 at low micromolar concentrations in prostate cell lines, reduce lamellipodia formation and cell migration, reduce invasion, and reduce metastasis or prostate cancer cells. According to one aspect of this disclosure, we have identified certain disulfonamides, having formulae as set forth below, or pharmaceutically acceptable salts thereof, that advantageously may be used to treat and/or prevent metastasis in mammals:

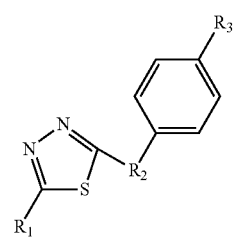

where $R_1$ is selected from the group consisting of —H or $C(CH_3)_3$, $R_2$ is selected from the group consisting of —SO$_2$NH, —SCH$_2$—CO—CH$_2$ and —CONH; and $R_3$—NH—CO—(CH$_2$)$_8$CH$_3$, and analogs thereof.

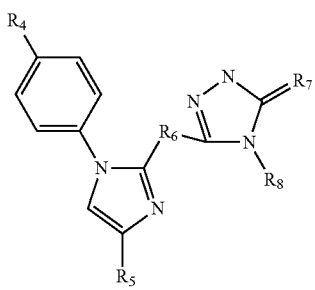
IIA

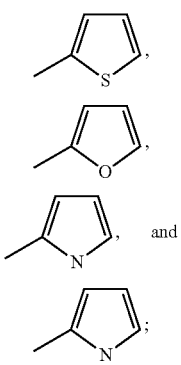
IIB where R$_4$ is selected from the group consisting of —H, —CH$_3$, and —CH$_2$CH$_2$;

R$_5$ is —H or a five or six member ring selected from the group consisting of

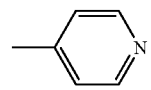

R$_7$ is selected from the group consisting of —H, =O, =S; and

R$_6$ is selected from the group consisting of —SCH$_2$—, —COCH$_2$—, —CONH—, or —CH$_2$CH$_2$—;

R$_8$ is selected from the group consisting of —CH$_3$, CH$_2$CH$_2$NH$_2$, —CH$_2$—C$_6$H$_5$, CH$_2$COOH,

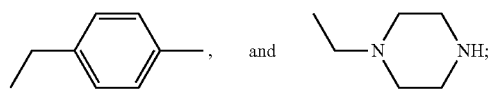

and analogs thereof.

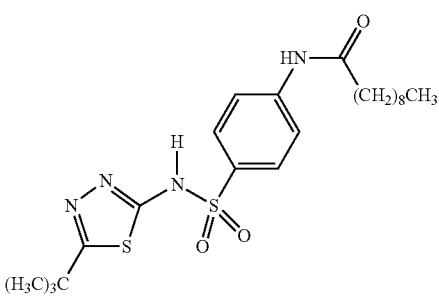
III where R$_9$ is selected from the group consisting of —H, and —CH$_3$; and R$_{10}$ is selected from the group consisting of and analogs thereof.

Another aspect of the disclosure relates to a method for treating a mammal at risk for developing metastasis, with a compound of formulae I, IIA, IIB or III as set forth above. The described treatment can be administered prophylactically or therapeutically. The described treatment also can be administered to a mammal having a metastatic condition to inhibit further metastasis.

In a preferred aspect of the disclosure, the compound administered comprises one or more of

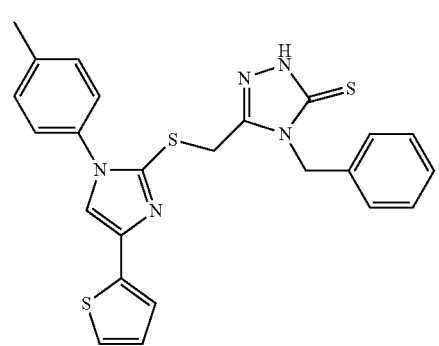
IV

V

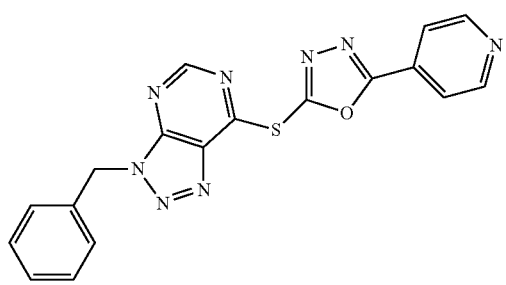
VI
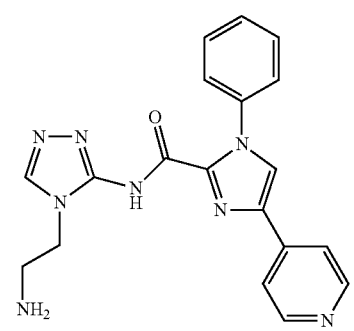
VII
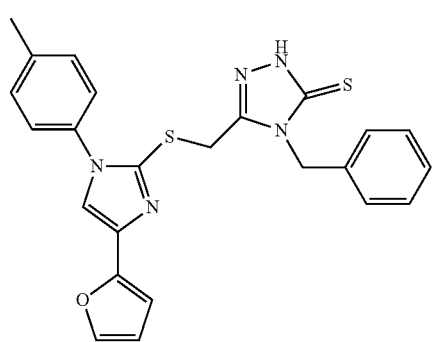
VIII
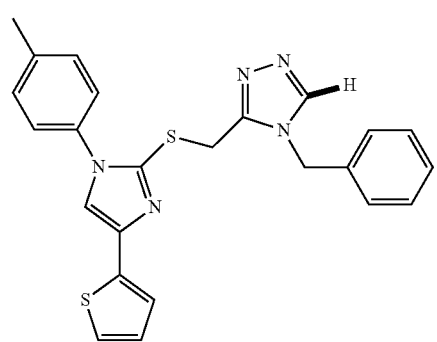
IX
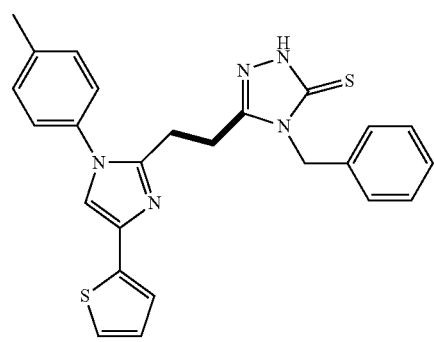
X
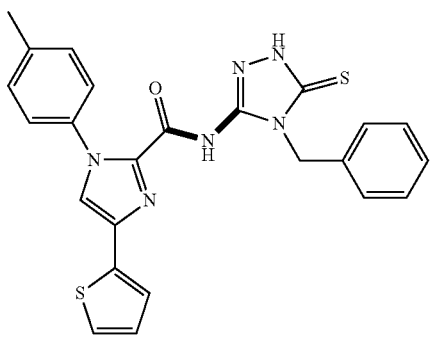
XI
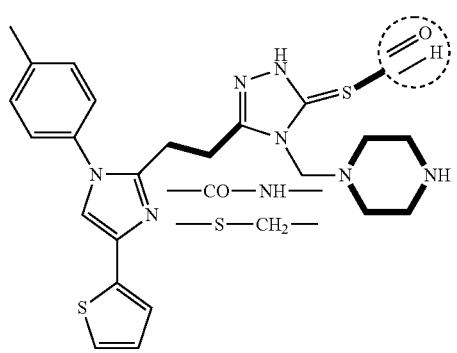
XII
—CO—NH—  
—S—CH₂—
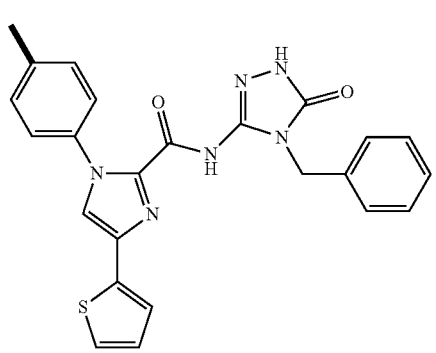
XIII
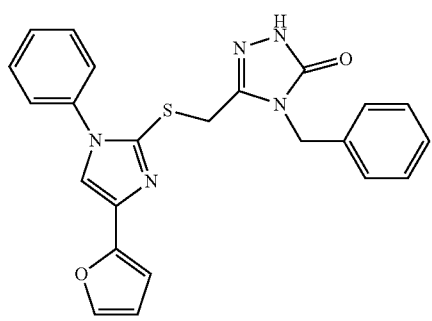
XIV

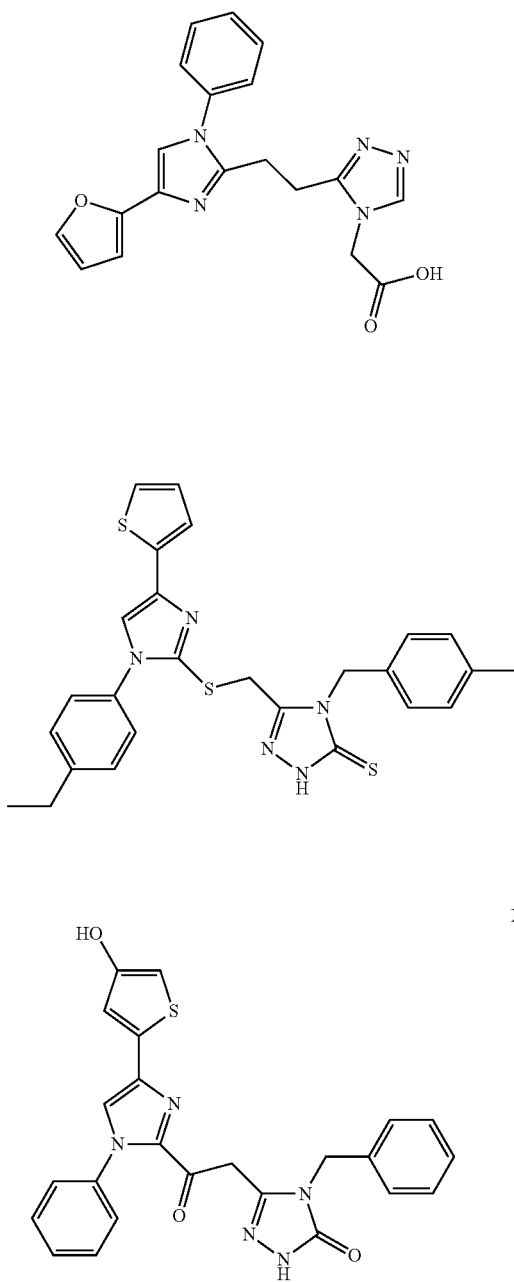

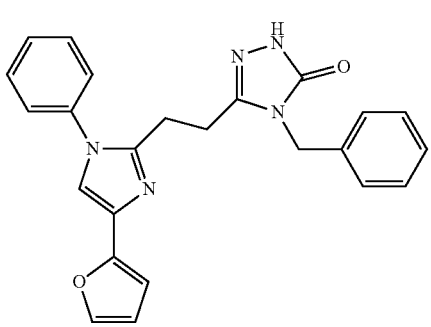

The disclosure in another aspect relates to a method for predicting the likelihood of development of a metastatic condition in a mammal, comprising the steps of obtaining a biological sample from the mammal to be tested; determining the Tiam-1 level (the test level), and comparing the test level with an appropriate control, wherein if the test level is greater than the level of the Tiam-1 product in a normal sample, then the mammal has an increased likelihood of developing a metastatic condition. The control can be a sample from a normal mammal or sample from a mammal having a metastatic condition.

In a specific embodiment, the metastatic condition is selected from one consisting of metastatic form of prostate cancer.

Further features and advantages of the present disclosure will be seen from the following detailed description, taken in conjunction with the accompanying drawings wherein, FIG. 1, Panels A-D illustrate how Tiam-1 is over-expressed in prostate cancers, and correlates with PTEN deletion and poor prognosis;

Figure 5B:
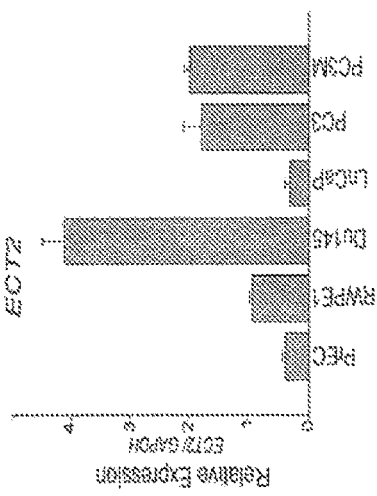
Figure 5C:
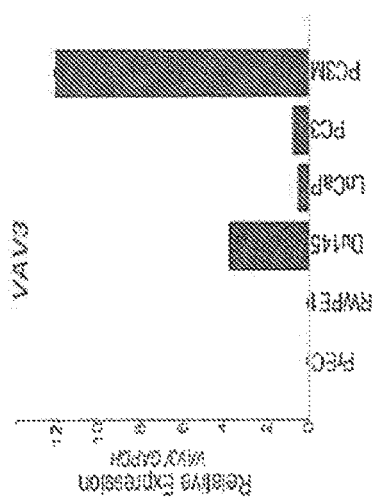
Figure 5A:
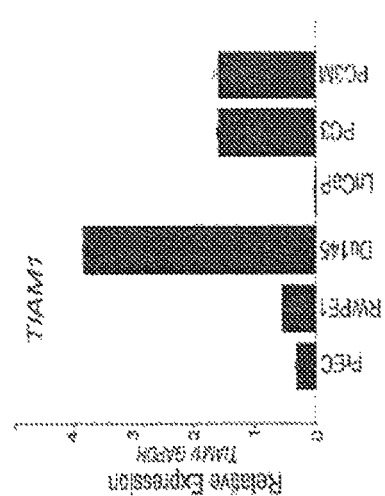

FIG. 3 Panels A-C show Tiam-RNA silencing;

FIG. 4 Panels A-D show how shRNA TIAM1 and compound V and VI inhibits lamellipodia formation, motility, invasion, colony formation and 2D migration (wound healing) of prostate cancer cells; and FIG. 5 Panels A-C show expression profiles of Tiam-1, ECT2 and VAV3, respectively following administration of the compound IV.

Before the compositions and methods of the disclosure are described, it is to be understood that this disclosure is not limited to the particular processes, compositions, or methodologies described, as these may vary. It is also to be understood that the terminology used in the description is for the purpose of describing the particular versions or embodiments only, and is not intended to limit the scope of the present disclosure which will be limited only by the appended claims.

It must be noted that, as used herein, and in the appended claims, the singular forms "a", "an" and "the" include plural reference unless the context clearly dictates otherwise. Unless defined otherwise, all technical and scientific terms used herein have the same meanings as commonly understood by one of ordinary skill in the art. Although any methods similar or equivalent to those described herein can be used in the practice or testing of embodiments of the present disclosure, the preferred methods are now described. All publications and references mentioned herein are incorporated by reference. Nothing herein is to be construed as an admission that the disclosure is not entitled to antedate such disclosure by virtue of prior disclosure.

As used herein, the term "about" means plus or minus 10% of the numerical value of the number with which it is being used. Therefore, about 50% means in the range of 45%-55%.

"Optional" or "optionally" may be taken to mean that the subsequently described structure, event or circumstance may or may not occur, and that the description includes instances where the event occurs and instances where it does not.

"Administering" when used in conjunction with a therapeutic means to administer a therapeutic directly into or onto a target tissue or to administer a therapeutic to a patient whereby the therapeutic positively impacts the tissue to which it is targeted. "Administering" a composition may be accomplished by oral or rectal administration, injection, infusion, inhalation, absorption or by any method in combination with other known techniques. Such combination techniques include heating, radiation and ultrasound.

The term "target", as used herein, refers to the material for which either deactivation, rupture, disruption or destruction or preservation, maintenance, restoration or improvement of function or state is desired. For example, diseased cells, pathogens, or infectious material may be considered undesirable material in a diseased subject and may be a target for therapy.

Generally speaking, the term "tissue" refers to any aggregation of similarly specialized cells, which are united in the performance of a particular function.

The term "improves" is used to convey that the present disclosure changes the appearance, form, characteristics and/or physical attributes of the tissue to which it is being provided, applied or administered. "Improves" may also refer to the overall physical state of an individual to whom an active agent has been administered. For example, the overall physical state of an individual may "improve" if one or more symptoms of a neurodegenerative disorder are alleviated by administration of an active agent.

As used herein, the term "therapeutic" means an agent utilized to treat, combat, ameliorate or prevent an unwanted condition or disease of a patient.

The terms "therapeutically effective amount" or "therapeutic dose" as used herein are interchangeable and may refer to the amount of an active agent or pharmaceutical compound or composition that elicits a biological or medicinal response in a tissue, system, animal, individual or human that is being sought by a researcher, veterinarian, medical doctor or other clinician. A biological or medicinal response may include, for example, one or more of the following: (1) preventing a disease, condition or disorder in an individual that may be predisposed to the disease, condition or disorder but does not yet experience or display pathology or symptoms of the disease, condition or disorder, (2) inhibiting a disease, condition or disorder in an individual that is experiencing or displaying the pathology or symptoms of the disease, condition or disorder or arresting further development of the pathology and/or symptoms of the disease, condition or disorder, and (3) ameliorating a disease, condition or disorder in an individual that is experiencing or exhibiting the pathology or symptoms of the disease, condition or disorder or reversing the pathology and/or symptoms experienced or exhibited by the individual.

The term "treating" may be taken to mean prophylaxis of a specific disorder, disease or condition, alleviation of the symptoms associated with a specific disorder, disease or condition and/or prevention of the symptoms associated with a specific disorder, disease or condition. In some embodiments, the term refers to slowing the progression of the disorder, disease or condition or alleviating the symptoms associated with the specific disorder, disease or condition. In some embodiments, the term refers to slowing the progression of the disorder, disease or condition. In some embodiments, the term refers to alleviating the symptoms associated with the specific disorder, disease or condition. In some embodiments, the term refers to restoring function, which was impaired or lost due to a specific disorder, disease or condition.

The term "patient" generally refers to any living organism to which to compounds described herein, are administered and may include, but is not limited to, any non-human mammal, primate or human. Such "patients" may or may not be exhibiting the signs, symptoms or pathology of the particular diseased state.

The term "pharmaceutical composition" shall mean a composition including at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan. A pharmaceutical composition may, for example, contain an AKT inhibitor or a pharmaceutically acceptable salt of an AKT inhibitor as the active ingredient.

For the purposes of this disclosure, a "salt" is any acid addition salt, preferably a pharmaceutically acceptable acid addition salt, including but not limited to, halogenic acid salts such as hydrobromic, hydrochloric, hydrofluoric and hydroiodic acid salt; an inorganic acid salt such as, for example, nitric, perchloric, sulfuric and phosphoric acid salt; an organic acid salt such as, for example, sulfonic acid salts (methanesulfonic, trifluoromethane sulfonic, ethanesulfonic, benzenesulfonic or p-toluenesulfonic), acetic, malic, fumaric, succinic, citric, benzoic, gluconic, lactic, mandelic, mucic, pamoic, pantothenic, oxalic and maleic acid salts; and an amino acid salt such as aspartic or glutamic acid salt. The acid addition salt may be a mono- or di-acid addition salt, such as a di-hydrohalogenic, di-sulfuric, di-phosphoric or di-organic acid salt. In all cases, the acid addition salt is used as an achiral reagent which is not selected on the basis of any expected or known preference for interaction with or precipitation of a specific optical isomer of the products of this disclosure.

"Pharmaceutically acceptable salt" is meant to indicate those salts which are, within the scope of sound medical judgment, suitable for use in contact with the tissues of a patient without undue toxicity, irritation, allergic response and the like, and are commensurate with a reasonable benefit/risk ratio. Pharmaceutically acceptable salts are well known in the art. For example, Berge et al. (1977) J. Pharm. Sciences, Vol 6. 1-19, which is hereby incorporated by reference in its entirety, describes pharmaceutically acceptable salts in detail.

As used herein, the term "daily dose amount" refers to the amount of pramipexole per day that is administered or prescribed to a patient. This amount can be administered in multiple unit doses or in a single unit dose, in a single time during the day or at multiple times during the day.

A "dose amount" as used herein, is generally equal to the dosage of the active ingredient, which may be administered per day. For example, an effective dose amount may be 10 mg/day to 10,000 mg/day.

The term "unit dose" as used herein may be taken to indicate a discrete amount of the therapeutic composition that contains a predetermined amount of the active compound. The amount of the active compound is generally equal to the dosage of the active ingredient, which may be administered one or more times per day. For example, the unit dose may be a fraction of the desired daily dose which may be given in fractional increments, such as, for example, one-half or one-third the dosage.

In the present disclosure, we demonstrate the use of in silico modeling to identify compounds that bind to the cPH domain of Tiam-1. The compounds found by this method were further tested by conventional biochemical and morphological tests, including in vitro experiments on prostate cancer cells to confirm disruption of Tiam-1 activity. Lead compounds were then subjected to a mouse xenograft model and a metastasis model to validate activity in vivo.

Materials and Methods

Human PCA Tissue Staining and cBio Portal Analysis.

Staining for Tiam-1 protein with anti-Tiam-1 primary antibody (Santa Cruz biotechnology Inc, Dallas Tx) was performed on a Benchmark Ultra automated stainer (Ventana Medical Systems, Inc Tucson, Ariz. VMSI). Briefly, 3 nm thick unstained sections of each study case were cut onto electrostatically charged glass slides (VWR superfrost slides). The Benchmark Ultra automated stainer includes on line deparaffinization and antigen retrieval. Anti-Tiam-1 Primary antibody was incubated for 32 minutes at 37 C. Antigen detection was performed using OPTIVIEW DAB IHC detection kit (VMSI) a peroxidase labeled streptavidin-biotin method and a diaminobenzidine chromogen step. Hematoxylin II (Ventana Medical Systems Inc) was used as a counterstain. All IHC scoring was performed using pathology long scores. Each stained tissue section was then scored for intensity staining on a 0-3+scale.

Kaplan-Meir plots were obtained from the Memorial Sloan-Kettering Cancer Center study [24] and analyzed using the cBIO portal [25].

PH Domain Structure Preparation for Docking.

Molecular docking was employed to study the interactions between the cPH domain of Tiam-1 and small molecule inhibitors. The target crystal structure (1FOE) [26] was retrieved from Protein Data Bank (PDB) for docking simulations. SYBYL computational information software was utilized to prepare the protein structures and default parameters were applied unless stated otherwise. Based on the mutation analysis [27], loop β12 and β34 are involved in the binding with phosphatidylinositol 3-phosphate (PtdInsP$_3$); Lys-1286 and Arg-1330 are two residues located on the β12 and β34 loop. In addition, Lys-1286 to Glu mutation looses the binding of PtdInsP$_3$[27], therefore, the binding site was defined as all residues within 10 Å from the centroid of Lys-1286 and Arg-1330. In order to further characterize residues critical for ligand binding, the binding site of Tiam-1cPH domain was investigated with GRID. For GRID calculation, a grid box was constructed to enclose the target with 1 Å beyond each dimension; molecular interaction fields (MIFs) were computed with three probes: the hydrophobic (DRY), the nitrogen atom (N, H-bond acceptor), and the water molecule (OH2, H-bond donor). Local energy minima were derived for these three MIFs so that the corresponding residues could be identified to analyze the interactions between the protein and the small molecule ligands.

Virtual Screening.

A high-throughput docking-based screening scheme, HiPCDock was employed to screen our in-house database of 10 million compounds to identify novel small molecule inhibitors binding to the cPH domain of Tiam-1 [28, 29]. The 3D structures of these small molecules were obtained using MOE software as follows: Hydrogen atoms were added and the protonation state of ionizable groups was calculated. The structures were then subjected to energy minimization using the MMFF94s force field with 0.05 kcal/mol as the threshold for the root mean square gradient.

Expression of Recombinant cPH of Tiam-1P.

Recombinant mouse Tiam-1 cPH domain amino acids 1261-1397 (UBI/Millipore, Charlottesville, Va.) was cloned by PCR into EcoRI/Not1 sites in pET-30b+ inducible bacterial expression plasmid (Novagen, Gibbstown, N.J.) transformed into BL21(DE3) *E. Coli*. Expression and purification of the protein were performed as described in reference [30].

Three compounds of particular interest were identified:

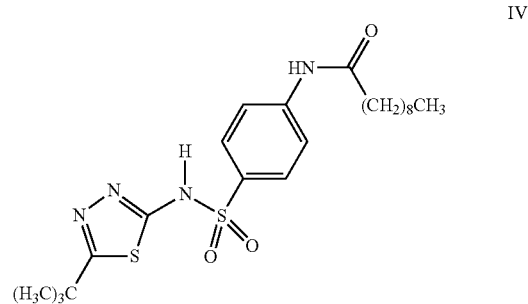

IV

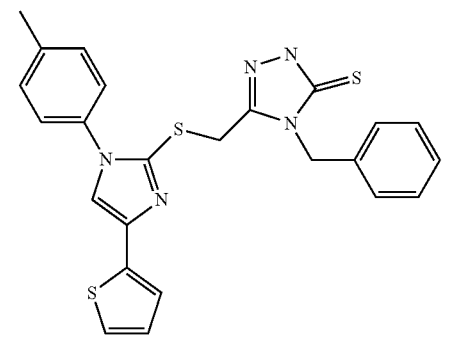

V

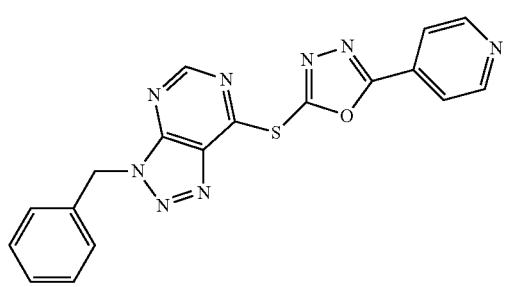

VI

Compound IV was synthesized following the procedure described in Ahad et al, Development of Sulfonamide AKT PH Domain Inhibitors, Bioorg MedChem, 2011.19(6):p. 2046-2054. 3088502 [31].

Surface Plasmon Resonance (SPR) Spectroscopy Binding Assays.

Interaction analyses were performed with a Biacore 2000, using the Biacore 2000 Control Software v3.2 and BIAevaluation v4.1 analysis software (Biacore, Piscataway, N.J.). The cPH domain GST-fusion Tiam-1 protein was immobilized on a CM5 Sensorchip (Biacore BR-1000-12) using Biacore's Amine Coupling Kit (Biacore BR-1000-50) to a level of 10,000 Response units (RUs). Small molecule analytes at concentrations ranging from one tenth to ten times the predicted $K_D$ were injected at a high flow rate (30 μL/min). Dimethylsulfoxide (DMSO) concentrations in all samples and running buffer were 1% (v/v) or less. For the competitive binding assays and the Ki determination, PtdIns 3,4,5-phosphates-biotin labeled liposomes (Echelon Biosciences, Salt Lake City, Utah) and SA chips were used with increasing concentrations of the compound tested as described in reference [30].

Cell Culture and Drug Treatments.

Human PC-3, LNCaP and DU145 prostate cancer cells were obtained from the American Type Culture Collection (Rockville, Md.). PC-3 cells were maintained in bulk culture in Dulbecco's modified Eagle medium/F12 (DMEM/F12), LNCaP were maintained in RPMI-1640, and DU145 maintained in DMEM. Each respective complete media was supplemented with 10% heat-inactivated fetal bovine serum (FBS), 4.5 g/L glucose, 100 U/mL penicillin and 100 μg/mL streptomycin in a 5% $CO_2$ atmosphere. Cells were passaged using 0.25% trypsin and 0.02% EDTA. Cells were confirmed to be mycoplasma free by testing them with an ELISA kit (Roche-Boehringer Mannheim, Indianapolis, Ind.). The cell lines were authenticated by our Shared Core Facility. Drugs were freshly prepared in DMSO at a stock concentration of 20 mM and then added at various concentrations (as indicated in the figures and/or figure legends) directly into the culture media of the cells.

Lentiviral Particle and Stable Cell Line Generation.

PC-3 cells were transfected with Tiam-1 shRNA lentiviral transduction particles according to the manufacturer's instructions (Sigma-Aldrich, Saint Louis, Mo.). Two independent shRNA sequences in pLKO.1 expression vector were used to transfect the cells resulting in creation of two cell lines called GS-1 and GS-2. GS-1 cell line was created from construct TRCN0000256946 (CCGGGTTGGTC-GAATTGTCTTAGAACTCGAGTTCTAAGACAATTC-GACCAAC TTTTTG) and the GS-2 cell line from construct TRCN0000018357 (CCGGCCTGAGGATGCGGATATA-GATCTCGAGATCTATATCCGCATCCTCAGG TTTTTG). As a control, an empty pLKO.1 vector was used to transfect the PC-3 cells. All resulting GS-1, GS-2 and control cells were selected from a single cell colony for each particular construct and puromycin (2 μg/ml) was used as a selective agent since the pLKO.1 vector contains the region for resistance to puromycin.

Lamellipodia Forming Assay.

Glass coverslips were sterilized with 100% EtOH and placed in 6-well plates. PC-3 cells, pKLO.1, GS-1 and GS-2 cells were plated at 3000 cells/well and allowed to adhere overnight. Cells where then serum starved for 48 hours, then treated with the indicated drug for 12 hours, and stimulated with 20% FBS for 30 minutes. Coverslips were then removed from the plates, washed twice with cold PBS, and fixed with 3.7% paraformaldehyde solution in PBS for 10 minutes. Cells were then permeabilized using 0.1% Triton X-100 for 5 minutes. Cells were stained with rhodamine phalloidin (Invitrogen, Carlsbad, Calif.) for 20 minutes using the supplied protocol. Coverslips were then air-dried and mounted using ProLong Gold with DAPI (Invitrogen, Carlsbad, Calif.) and stored at 4° C. Cells were visualized at 40× using Olympus Bx-50 microscope with the CellSens imaging software. Individual lamellipodia were counted in a minimum of 10 cells in each respective group and statistical analysis was done using a Student's t-test.

Rac1 Activation Assay.

Rac1 activity was determined by the colorimetric GLISA Kit BK128 (Cytoskeleton, Inc, Denver, Co). Briefly, PC-3 (PC-3, pKLO.1, GS-1 and GS-2 cells), DU 145 and LNCap cells were grown to 75% confluence and then serum starved for 48 hours. Drugs were then added for 4 hours and cells were stimulated with 50 ng/ml hHGF (Gibco Life Sciences, Carlsbad, Ca) for 2 minutes. Cells were then lysed and harvested as described in the kit-supplied protocol. Protein concentration was normalized to 1.0 g/l. Plates were read in an absorbance spectrophotometer at 490 nm at 24° C. with 5 s medium orbital shaking. Data were analyzed as described in the supplied protocol. The results represent an average of three independent experiments, each run in duplicates.

Migration Wound Closure Assay.

PC-3, DU145 and LNCaP cells were grown in six-well plates in the presence of 10% FBS. Once the cells formed a monolayer, near confluency a wound was done manually with a sterile 1000 L pipette tip in the center of each well. Cells were treated with vehicle alone (DMSO) or 10 μM of compound IV and were grown in the presence of 2% FBS. After 18 hours, the migrating cells were photographed. The wound closure was quantified by measuring the distance between the two sides of the wound. The results represent an average of two independent experiments, each run in triplicates.

RNA Extraction and Quantitative Real-Time Reverse Transcriptase Polymerase Chain Reaction (RT-PCR).

RNA extraction from all isogenic variants was performed using RNAeasy kit (Qiagen, Valencia, Calif.). Human Tiam-1 (Hs.517228) and GAPDH (Hs99999905_A1) primer/probes were bought from ABI (Applied Biosystems, Branchburg, N.J.). cDNA was synthesized from 500 ng of total RNA in a 50 µl reaction with master mix containing 10×RT buffer, 5.5 mM $MgCl_2$, 2 mM dNTPs, 2.5 µM random hexamers, 2 Units of RNase Inhibitor and 62.5 Units of Multi Scribe Reverse Transcriptase. All MasterMix reagents were purchased from ABI (Applied Biosystems, Branchburg, N.J.). Reactions were performed in MJ Thermocycler PTC-200 (MJ Research, Inc., Watertown, Mass.) at 25° C. for 10 minutes, 48° C. for 30 minutes and 95° C. for 5 minutes. 2 it of 5 ng/l cDNA was then used to amplify the human Tiam-1 sequence. The conditions for PCR reactions were: 10 minutes at 95° C. followed by 15 seconds at 95° C., 1 minute at 60° C. for 40 cycles by using ABI7000 real-time PCR machine (InVitrogen). PCR amplification of the human GAPDH was used to control quality of the cDNA. Non-template controls were included on each PCR plate. Tiam-1 levels were normalized to the GAPDH control. Amplification plots were generated and the $C_t$ value (cycle number at which fluorescence reaches threshold) were recorded.

Cell Cytotoxicity Assay.

A standard 96-well micro-cytotoxicity assay was performed by plating cells at 5,000-10,000 cells/well (depending on cell doubling time) for a growth period of 4 days. TPH compounds were added directly to the media of PC-3, DU145 and LNCaP cells, dissolved in DMSO at various concentrations ranging from 1 to 200 µM. The endpoint was the spectrophotometric determination of the reduction of 3-(4,5-dimethylthiazol-2-yl)-2,5-diphenyltetrazolium bromide as described previously [30]. The results represent an average of two independent experiments, each run in quadruplates.

Colony Formation Assay.

PC-3, LNCaP and DU145 cells were plated at 1000 cells/well into standard 6-well plates (3.5 cm) in the presence of complete media. The next day cells were drugged at increasing concentrations ranging from 1 to 50 µM in triplicate wells. Cells were viewed twice weekly to check for colony growth and confluence. Media and respective drugs were carefully replaced every three days. At day 12, media was aspirated and resulted colonies were stained with crystal violet (0.5% w/v) dissolved in ethanol for one minute, washed with water, and air dried as already described in reference [32]. The resulting colonies were counted utilizing an Optronix Colony counter using ColCount software (Oxford Optronix Ltd, UK). The results represent an average of two independent experiments, each run in triplicates.

Matrigel Invasion Assay.

PC-3 cells were pre-treated with DMSO vehicle control or with drug for 4 hours in T-25 flasks. Thereafter, 50,000 cells were then plated into the upper chamber that has been pre-coated with Matrigel (BD Sciences, San Jose, Ca) in the presence of drug or DMSO and serum-free media. The bottom well contained complete media including 10% FBS and 0.5% BSA as chemoattractants. After 24 hours, the upper chambers were removed, and any remaining cells within the insert were wiped with a cotton swab. Invading cells were then stained with 2% crystal violet in 20% methanol. Cells were then counted using a Zeiss stereomicroscope at 20× power. 10 random fields were counted. The results represent an average of two independent experiments, each run in triplicates.

Statistical Analyses.

Data are presented as mean±S.E. Statistical analyses (Student's two-tailed t-tests) were performed using Stata software (Stata Corporation, College Station, Tex.).

Results:

Tiam-1 Expression Correlates with PTEN Loss in the Primary Tumor and the Metastases of a Subset of PCA Tumors.

Tiam-1 has been shown to be over-expressed in PCA where it is an independent predictor of decreased disease free survival [19]. Over-expression of Tiam-1 is associated with increased metastatic potential in PCA cell lines [19, 34, 35]. In this study, we investigated the potential role for Tiam-1 in CRPCA. We performed immunohistochemistry on human PCA tissue samples for Tiam-1 (FIG. 1) which shows Tiam-1 is over-expressed in prostate cancers, correlates with PTEN deletion and poor prognosis. Panel A, Tiam-1 localization in primary human PCAs tissue samples. (A) low-grade 3+3, 20×; (B) 40× magnification of 3+3 showing localization at cell-cell junctions (note arrow); (C) high grade 4+4; (D) mixed tumors 3+ and 4+. Panel B represents the quantification of the staining from the representative samples shown in Panel A. Panel C, Kaplan-Meir plot obtained from the cBIO portal [25]. The gene set which was analyzed is PTEN/Tiam-1 in human primary tumors. Panel D represents the same gene set for human metastases tissues. If both genes are altered, patients exhibited a worse prognosis. Our results revealed that Tiam-1 expression correlates with PTEN loss and with recurrence. It also correlates with capsular penetration and aggressiveness of the tumors. Kaplan-Meir plots issued from the Memorial Sloan-Kettering Cancer Center (MSKCC) study analysis [24] showed an association and correlation between PTEN loss and Tiam-1 over-expression in both primary (Panel C) and metastases (Panel D) PCAs.

In Silico Screen for Compounds that Bind to the cPH Domain of Tiam-1.

In our previous studies, GOLD docking and its scoring function were reported to be the best combination for the analysis of PH domain-small molecule inhibitor interactions [30]. Therefore, the GOLD docking engine integrated in HiPCDock® was employed for virtual screening. The Tiam-1 protein was treated as rigid and the flexibility of the ligand was explored. Internal hydrogen bonds were included to restrict the flexibility, and no early termination was allowed. Other default docking parameters were applied. After virtual screening, chemical diversity analysis was conducted for the top 5,000 hits using MOE and the best-scored hit from each cluster was selected for the second round docking with flexible target. The top 100 hits were visualized to inspect the binding mode and protein-ligand interactions. Also taken into consideration were the physicochemical properties of the compounds to predict potential "drug-likeness"[36]. We used Lipinski's "Rule of Five" which takes into account a molecule's molecular weight, the LogP, and its ability to accept and donate hydrogen atoms in the formation of hydrogen bonds. In general, our potential top list of compounds fit within the criteria. By considering structural diversity, GOLD docking score and ligand binding poses, and some of the ADMET properties such as Caco-2 permeability, we selected 9 compounds for biological testing.

Analysis of the cPH Domain of Tiam-1 and Binding Characteristics of Selected Compounds.

The protein surface of Tiam-1 cPH domain was characterized using the Site Finder module in MOE8. The region between loop β12 and β34 was determined as the best potential site for the ligand binding. This is in agreement with published mutagenesis reports stating that loop β12 and β34 are involved in the binding with PtdInsP$_3$. In the cPH domain binding site, Arg-1330 was identified using GRID as a favorable place to interact with hydrogen acceptor; Asp-1306 and Arg-1330 as a preferential area for interacting with a hydrogen donor; and Phe-1331 and Tyr-1304 as a prior-ranking area for the hydrophobic interactions with the small molecule inhibitors. The defined active site of Tiam-1 cPH domain was used for hit identification via high-throughput virtual screening. Surface Plasmon Resonance (SPR) spectroscopy was used to validate our in silico predictions. The results are compiled. Three formulas of compounds (Formula I, II and III), all sulfonamides exhibited a strong binding to the cPH domain of Tiam-1 with a $K_D$ in the micromolar range. Interestingly, these results correlated well with a low GOLD score. Compounds with a GOLD score higher than 57 (except TPH-6), were shown to bind to the cPH domain of Tiam-1.

In Vitro Validation of Hits.

The selected compounds where then tested in vitro to assess their ability to reduce the levels of active Rac1 which shows GLISA assay screen for Rac1 inhibition. A cellular screen of all hit compounds was conducted using the GLISA Rac1 activation kit. Briefly, PC-3 cells were drugged for 4 hours at 1 μM concentration with the selected compounds. Cells were then stimulated with 50 ng/ml of hHGF for 2 minutes. Compounds V and VI showed the most pronounced and significant reduction of active Rac1, to reduce lamellipodia formation, to reduce migration, and to reduce invasion in PCA cells. The isovolume of Tiam-1 PH domain (PDB 1FOE) was generated using GRID for the H-bond acceptor (−3.6 kcal/mol), the H-bond donor (−7.3 kcal/mol) and hydrophobic (−2.5 kcal/mol) probes. The critical residues are labeled around the isovolume surfaces. The dash lines represent hydrogen bonds between protein and inhibitors. (FIG. 3, Panel B), SPR sensorgrams for the binding of increasing concentrations of compound of Formula V to the cPH domain of Tiam-1. The concentrations of compound IV ranged from 0.5 μM for the lowest curve to 20 μM for the top curve.

Characterization of the Cellular Effects of the Compound of Formula IV in Prostate Cancer Cells.

As reported previously, inhibition of Tiam-1 and subsequent inactivation of downstream signaling proteins leads to reduced actin cytoskeleton rearrangements resulting in decreased cell motility [37]. Near-to-confluent PC-3 cells exhibited a significant inability to close a wound introduced by scratching after 18 hours when treated with 10 μM of the compound V (FIG. 4, Panel A). Similarly, Tiam-1 shRNA clone 1.2 was unable to close a scratch-induced wound (FIG. 4, Panel A) which shows the compound IV inhibits lamellipodia formation, motility, and invasion of PC-3 cells. FIG. 4, Panel A, A wound channel was introduced near-to-confluent non-treated or treated PC-3 cells with 10 μM V pKLO1 mock-transfection control cells, and shRNA cell line 1.2 (GS-1). Cells treated with the compound V, as well as cells containing shRNA against Tiam-1 exhibited a significant inability to close the wound as quantified in the graph. FIG. 4, Panel B, PC-3 cells and Tiam-1 shRNA cell line 1.2 (shRNA 1.2) were treated as indicated, then stimulated with 20% FBS for 20 minutes to induce lamellipodia formation and stained with rhodamin phalloidin. Individual lamellipodia were counted in a minimum of 10 cells in each respective group and statistical analysis was performed using a Student's t-test. A marked reduction of lamellipodia formation was observed in PC-3 cells treated with 10 μM the compound IV, and in the Tiam-1 shRNA 1.2 cell line. FIG. 4, Panel C, pKLO1 PC-3 cells, pKLO1 treated with 10 μM compound V and shRNA 1.2 cells were allowed to invade through Matrigel-coated transwell plates. Invading cells were stained after 12 hours and counted at 20× power (left side). Cells treated with the compound of Formula V and shRNA 1.2 cells exhibited a significantly reduced amount of invading cells relative to pKLO.1 cells. This suggests that cancer cells treated with the compound of Formula V and Tiam-1 knockdown cells may have reduced motility in two dimensions through a similar mechanism. In order to test our hypothesis, cells were stained with rhodamin phalloidin and then analyzed for actin/cytoskeleton formations, such as lamellipodia. Treatment of PC-3 cells with 10 μM of the compound of Formula V significantly reduced the frequency of lamellipodia formation after stimulation with 20% FBS (FIG. 4, Panel B). A similar effect was seen in Tiam-1 shRNA clone 1.2. Thus, the observed reduction in cellular motility in compound V treated cells and Tiam-1 silenced cells may be the result of f-actin disruption and reduced frequencies of lamellipodia formation. We next tested whether the compound of Formula V affected invasion of PC-3 through Matrigel-coated transwells. PC-3 cells treated with 10 μM of compound V exhibited reduced invasion in Matrigel invasion assay (FIG. 4, Panel C) and comparatively, Tiam-1 silenced cells exhibited a reduced invasion potential. Finally, the compound IV was able to reduce the colony forming abilities of PC-3, DU145 and LNCaP cells Taken together, these results demonstrate that, at concentrations close to 10 μM, compound IV reduces the cells capacities to migrate and invade with low toxicities (>30 μM).

Figure 1A:
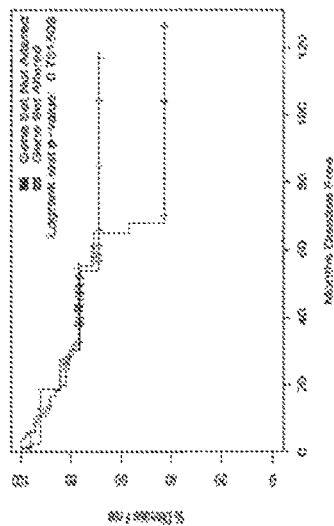
Figure 1C:
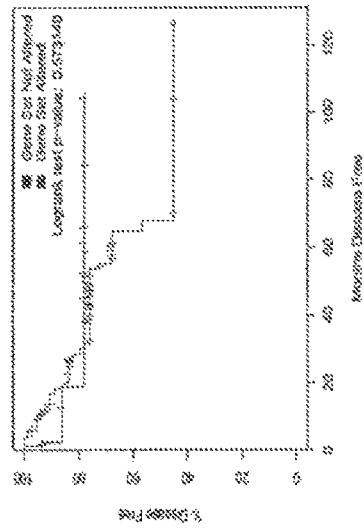
Figure 1B:
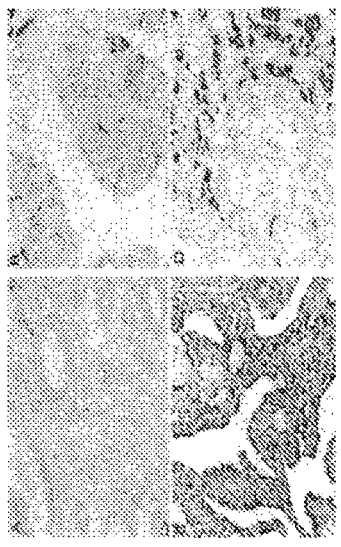
Figure 1D:
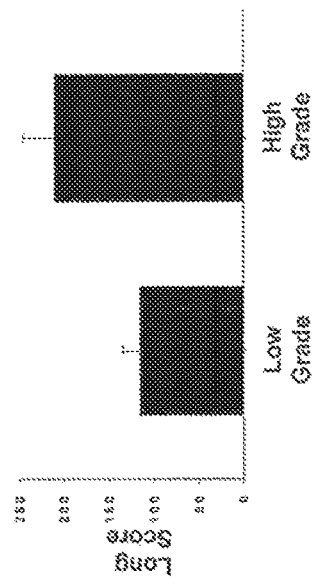
Figure 2A:
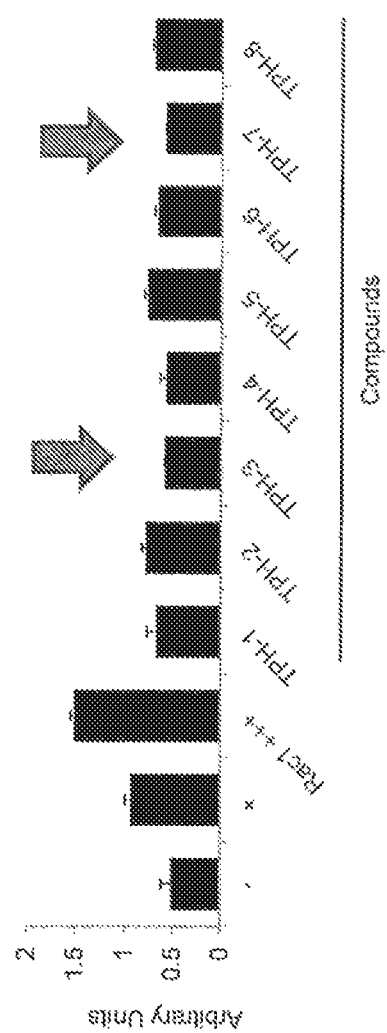
FIG. 2A is a GLISA assay screen for Rac1 inhibition of prostate cancer cells, where compound #3 is V and #7 is VI.
Figure 2B:
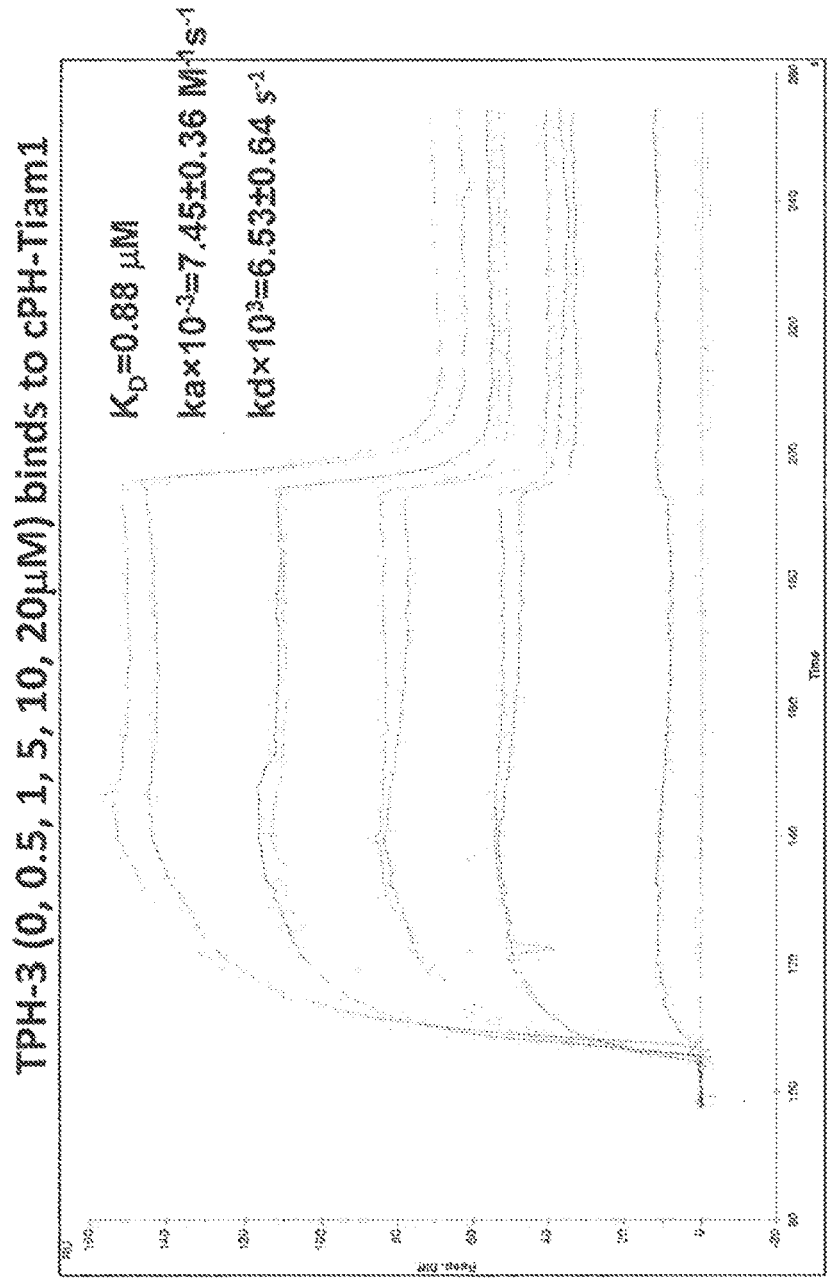
FIG. 2B shows how compound V bind to cPH domain of Tiam 1.
Figures 3A, 3B, 3C:
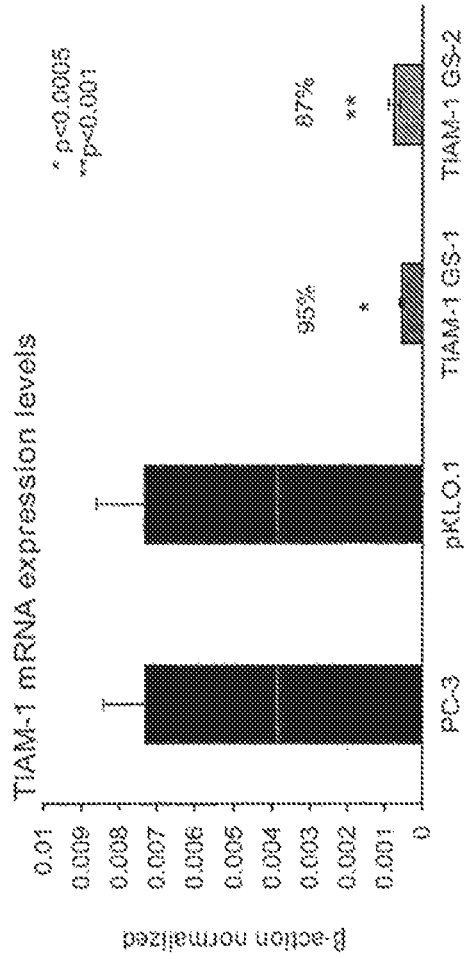
Figure 4A:
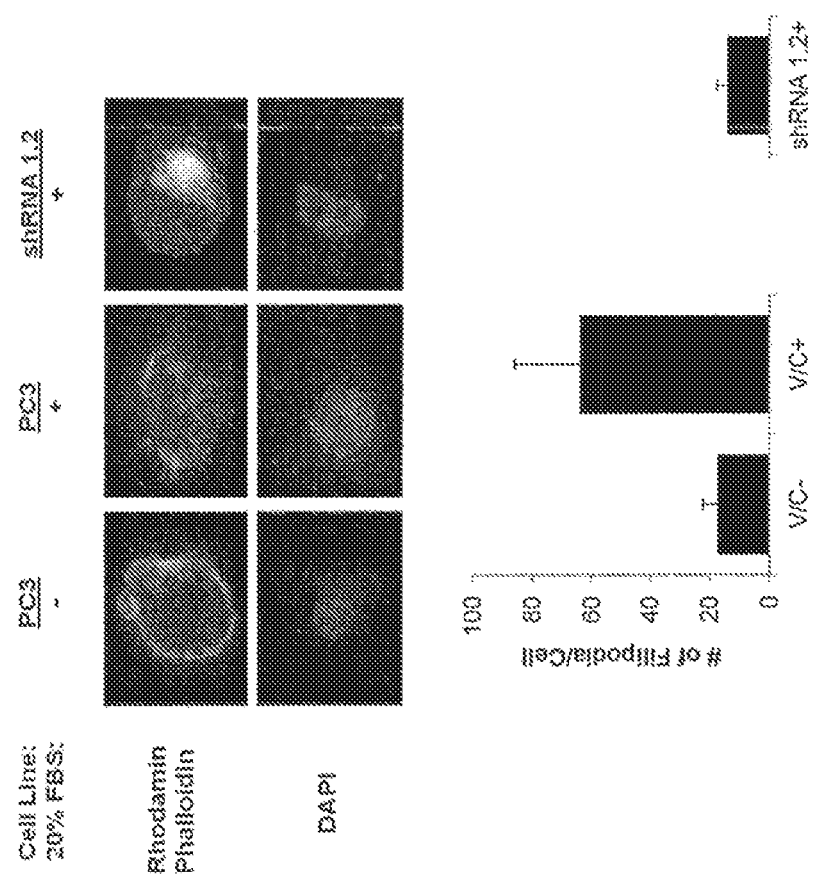
Figure 4B:
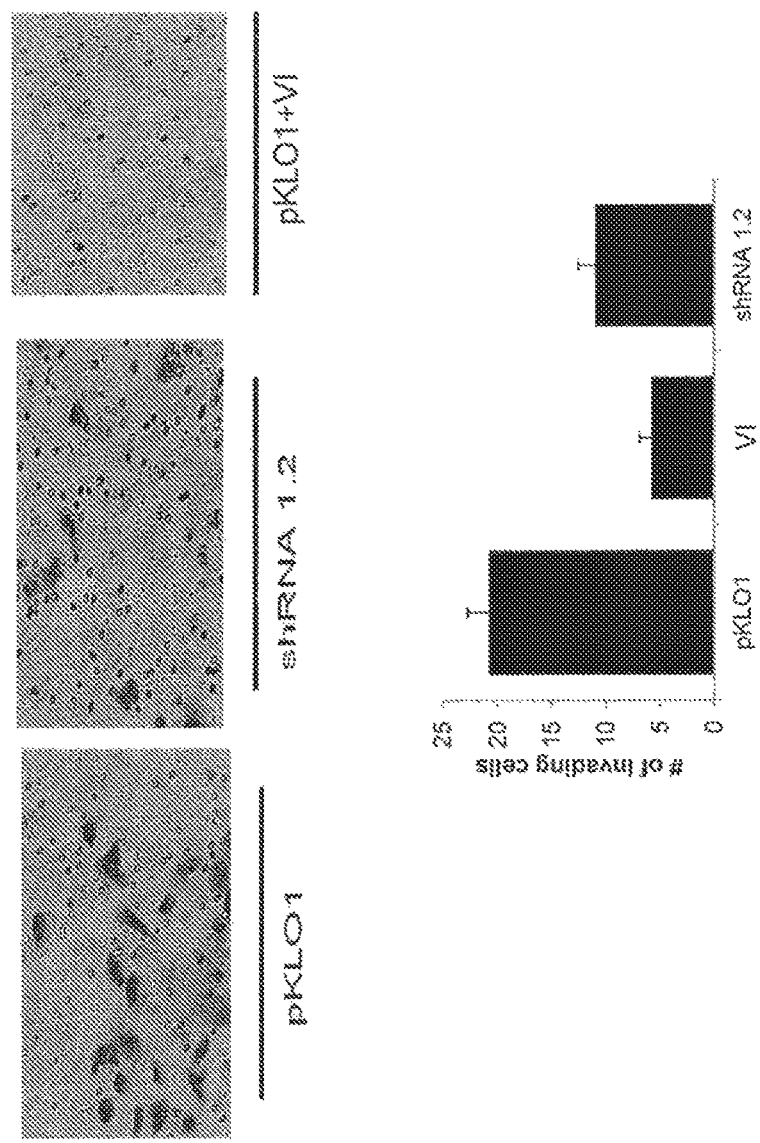
Figure 4C:
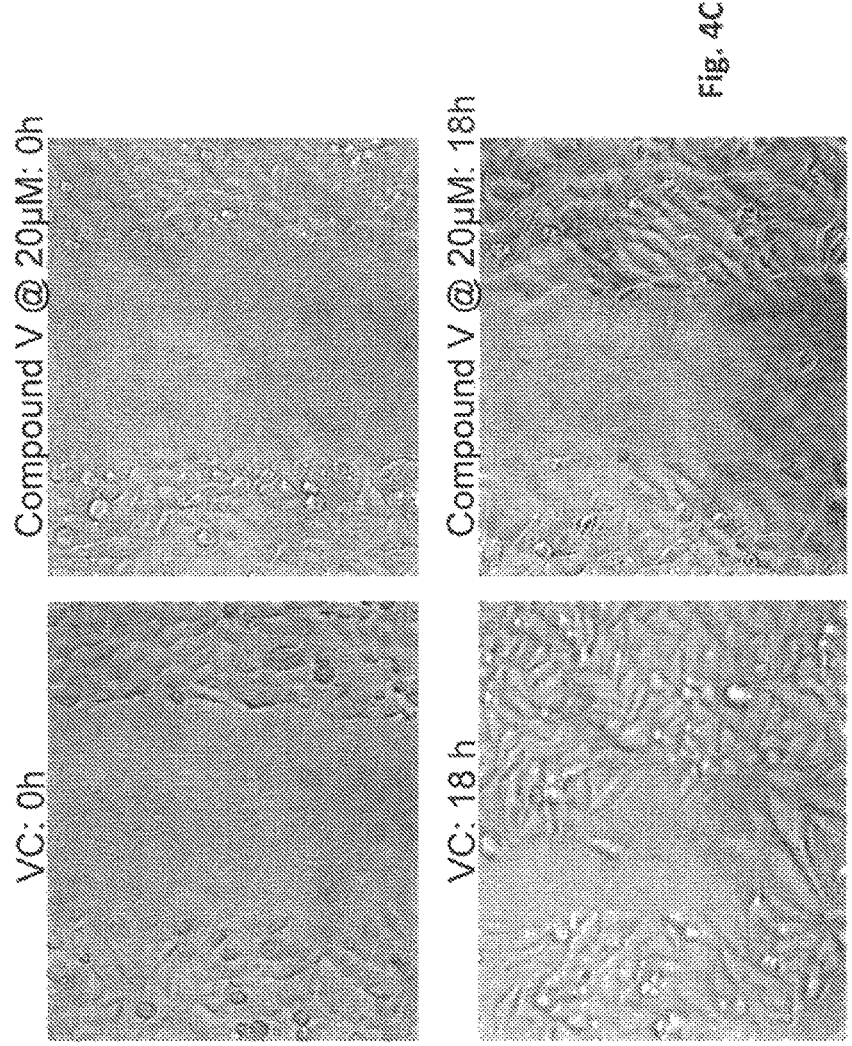
Figure 4D:
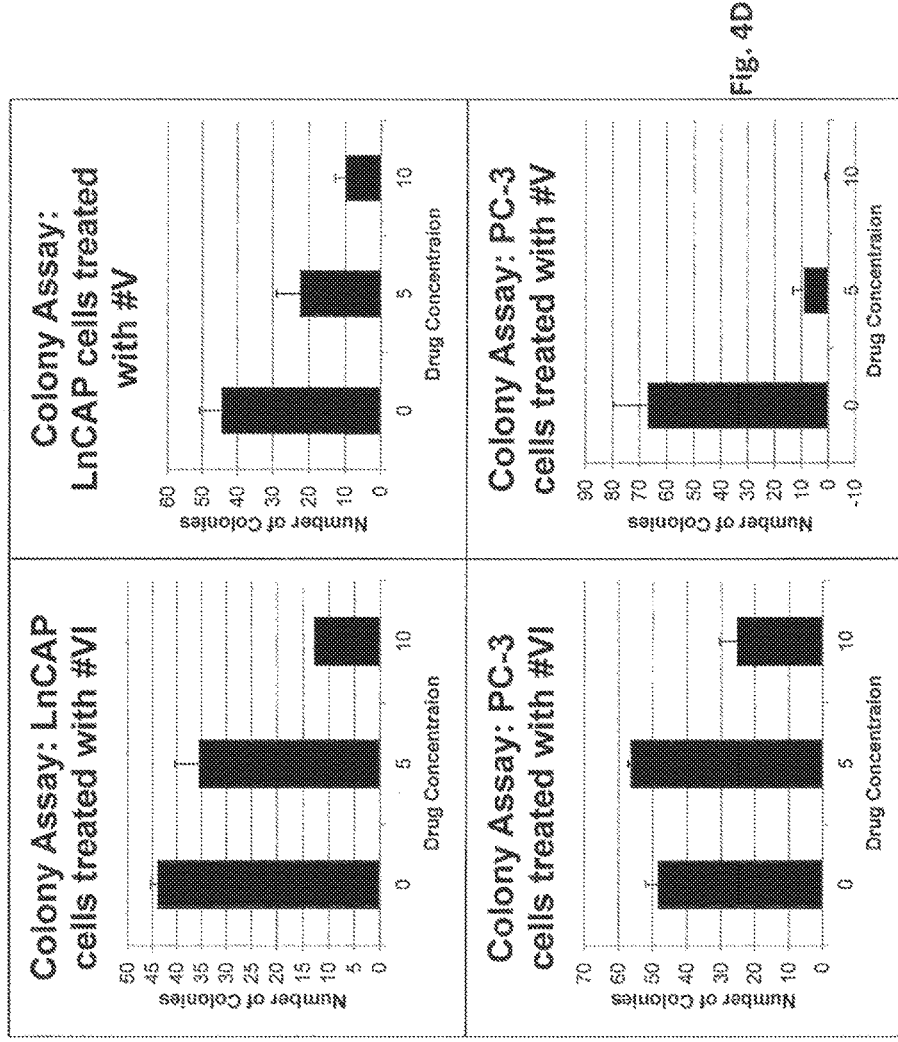

We investigated expression of other GEFs in normal and PCA cell lines and a select panel of other cancer cell lines for selectivity purposes, and determined that for qPCR PC-3 cell lines Tiam-1 is over-expressed (FIG. 3, Panels A and B). In order to test the role of Tiam-1 over-expression in PC-3 cells' characteristically aggressive metastatic behavior, we created a series of PC-3 cells that have been lentivirally transduced with shRNA against Tiam-1. Two of the PC-3 shRNA gene sequences, GS-1 and GS-2, exhibited excellent Tiam-1 RNA silencing as verified by qPCR while an empty vector control, pKLO1, did not reduce Tiam-1 RNA (FIG. 3, Panel A). Additionally, Western Blot analysis of the shRNA clones revealed that clone 1.2, a monoclonal colony harboring the GS-1 sequence, showed almost complete knockdown of Tiam-1 at the protein level (FIG. 3C, Panel C). Lastly, because Tiam-1 is a specific GNEF for the GTPase Rac1, we have used active Rac1 as a marker for Tiam-1 activity. We tested our shRNA clones for Rac1 activation by stimulating with human hepatocyte growth factor (hHGF). Clones 1.2 and X.X exhibited a minimal reduction of activated Rac1 as compared to parent PC-3 cells and the vector-only control (FIG. 3C, Panel D). PC-3 PCA cells exhibit an over-expression of several other Rac-specific GNEFs, including VAV3. Hence, we surmise that levels of activated RAC1 may be compensated by other Rac-GNEFs in the absence of Tiam-1. Levels of Tiam-1 RNA are highly increased in MDA-MB-231 and moderately increased in MCF-7 over HMEC cells. In each instance, levels of Tiam-1 correspond to increased metastatic potential as previously reported [34, 39]. FIG. 6 summarizes the expression profile of Tiam-1 (Panel A), of ECT2 (Panel B) and Vav3 (Panel C) of FIG. 6. Interestingly, the transcript levels of both ECT2 and Tiam-1 were similar in the cells tested by RT-PCR. Tiam-1 and ECT2 were highly expressed in DU-145, to a lesser extent in PC-3 and with very low levels in LNCaP cells. On the contrary, Vav3 expression was shown to be much higher in PC3M as compared to DU-145, with low expression levels in LNCaP cells.

In conclusion, we have identified certain small molecule compounds targeting cPH domain of Tiam-1. The compounds disclosed inhibited Tiam-1 GEF function and subsequent activation of its downstream targets. Results of an in vivo study showed that the compound IV reduced metastasis and increased survivability in prostate cancer cell cardio-injected in mice.

FIG. 6, Panels A-C shows the expression of other GEFs in prostate cancer cell lines.

Embodiments of the disclosure encompass stereoisomers and optical isomers of the compounds described above including, e.g., mixtures of enantiomers, individual enantiomers and diastereomers, which can arise as a consequence of structural asymmetry of atoms in the compounds of the disclosure. Such embodiments further include the purified enantiomers, which may or may not contain trace amounts of a non-selected enantiomer or diastereomer.

Embodiments of the disclosure also include salts of the compounds described above. In general, the term salt can refer to an acid and/or base addition salt of a compound. For example, an acid addition salt can be formed by adding an appropriate acid to a free base form of any of the compounds embodied above. Similarly, a base addition salts can be formed by adding an appropriate base to a free base form of any of the compounds described above. Examples of suitable salts include, but are not limited to, sodium, potassium, carbonate, methylamine, hydrochloride, hydrobromide, acetate, furmate, maleate, oxalate, and succinate salts. Methods for preparing free base forms of compounds such as those described herein and acid addition or base addition salts of such compounds are well known in the art, and any such method may be used to prepare the acid or base addition salts of embodiments of the disclosure.

Other embodiments of the disclosure include solvates or hydrates of the compounds of the disclosure. In some cases, hydration of a compound may occur during manufacture of the compounds or compositions including the compounds as a consequence of the method for preparing the compound or as a result of a specific step used to create a hydrate or solvate of the compound. In other cases, hydration may occur over time due to the hygroscopic nature of the compounds. Such hydrated compounds whether intentionally prepared or naturally produced are encompassed by the disclosure.

Embodiments of the disclosure also include derivatives of the compounds of the disclosure which may be referred to as "prodrugs." The term "prodrug" as used herein denotes a derivative of a known drug that may have enhanced delivery characteristics, enhanced therapeutic value as compared to the active form of the drug, sustained release characteristics, reduced side-effects, or combinations thereof. For example, in some embodiments, a prodrug form of a compound of the disclosure may be administered in an inactive form or a form having reduced activity that is transformed into an active or more active form of the drug by an enzymatic or chemical process. For instance, in some embodiments, a prodrug form of a compound such as those described above may include one or more metabolically cleavable groups that are removed by solvolysis, hydrolysis or physiological metabolisms to release the pharmaceutically active form of the compound. In other embodiments, prodrugs may include acid derivatives of the compounds of the disclosure. Acid derivatives are well known in the art and include, but are not limited to, esters or double esters such as, for example, (acyloxy) alkyl esters or ((alkoxycarbonyl)oxy)alkyl esters prepared by reaction of an acid on the parent molecule with a suitable alcohol. Without wishing to be bound by theory, the compounds of the disclosure may have activity in both their acid and acid derivative forms. However, the acid derivative form may exhibit enhanced solubility, tissue compatibility or delayed release in the mammalian organism (see, e.g., Bundgard, H., Design of Prodrugs, pp. 7-9, 21-24, Elsevier, Amsterdam 1985). In still other embodiments, prodrugs that include an amide may be prepared by reacting a parent compound containing an acid with an amine, and in yet other embodiments, simple aliphatic or aromatic esters derived from acidic groups pendent on a compound of this disclosure may be prepared as prodrugs.

Embodiments of the disclosure also include pharmaceutical compositions or formulations including at least one compound embodied hereinabove, an acid or base addition salt, hydrate, solvate or prodrug of the at least one compound and one or more pharmaceutically acceptable carriers or excipients. Pharmaceutical formulations and pharmaceutical compositions are well known in the art, and can be found, for example, in Remington's Pharmaceutical Sciences, Mack Publishing Co., Easton, Pa., USA, which is hereby incorporated by reference in its entirety. Any formulations described therein or otherwise known in the art are embraced by embodiments of the disclosure.

Pharmaceutical excipients are well known in the art and include, but are not limited to, saccharides such as, for example, lactose or sucrose, mannitol or sorbitol, cellulose preparations, calcium phosphates such as tricalcium phosphate or calcium hydrogen phosphate, as well as binders, such as, starch paste such as, for example, maize starch, wheat starch, rice starch, potato starch, gelatin, tragacanth, methyl cellulose, hydroxypropylmethylcellulose, sodium carboxymethylcellulose, polyvinyl pyrrolidone or combinations thereof.

In particular embodiments, pharmaceutical formulations may include the active compound described and embodied above, a pharmaceutically acceptable carrier or excipient and any number of additional or auxiliary components known in the pharmaceutical arts such as, for example, binders, fillers, disintegrating agents, sweeteners, wetting agents, colorants, sustained release agents, and the like, and in certain embodiments, the pharmaceutical composition may include one or more secondary active agents. Disintegrating agents, such as starches as described above, carboxymethyl-starch, cross-linked polyvinyl pyrrolidone, agar, alginic acid or a salt thereof, such as sodium alginate and combinations thereof. Auxiliary agents may include, for example, flow-regulating agents and lubricants, such as silica, talc, stearic acid or salts thereof, such as magnesium stearate or calcium stearate, polyethylene glycol and combinations thereof. In certain embodiments, dragee cores may be prepared with suitable coatings that are resistant to gastric juices, such as concentrated saccharide solutions, which may contain, for example, gum arabic, talc, polyvinyl pyrrolidone, polyethylene glycol, titanium dioxide, lacquer solutions and suitable organic solvents or solvent mixtures and combinations thereof. In order to produce coatings resistant to gastric juices, solutions of suitable cellulose preparations, such as acetylcellulose phthalate or hydroxypropylmethylcellulose phthalate may also be used. In still other embodiments, dye stuffs or pigments may be added to the tablets or dragee coatings, for example, for identification or in order to characterize combinations of active compound doses.

Pharmaceutical compositions of the disclosure can be administered to any animal, and in particular, any mammal, that may experience a beneficial effect as a result of being administered a compound of the disclosure including, but not limited to, humans, canines, felines, livestock, horses, cattle, sheep, and the like. The dosage or amount of at least one compound according to the disclosure provided pharmaceutical compositions of embodiments may vary and may depend, for example, on the use of the pharmaceutical composition, the mode of administration or delivery of the pharmaceutical composition, the disease indication being treated, the age, health, weight, etc. of the recipient, concurrent treatment, if any, frequency of treatment, and the nature of the effect desired and so on. Various embodiments of the disclosure include pharmaceutical compositions that include one or more compounds of the disclosure in an amount sufficient to treat or prevent diseases such as, for example, cancer. An effective amount of the one or more compounds may vary and may be, for example, from about 0.001 mg to about 1000 mg or, in other embodiments, from about 0.01 mg to about 100 mg.

The pharmaceutical compositions of the disclosure can be administered by any means that achieve their intended purpose. For example, routes of administration encompassed by the disclosure include, but are not limited to, subcutaneous, intravenous, intramuscular, intraperitoneal, buccal, or ocular routes, rectally, parenterally, intrasystemically, intravaginally, topically (as by powders, ointments, drops or transdermal patch), oral or nasal spray are contemplated in combination with the above described compositions.

Embodiments of the disclosure also include methods for preparing pharmaceutical compositions as described above by, for example, conventional mixing, granulating, dragee-making, dissolving, lyophilizing processes and the like. For example, pharmaceutical compositions for oral use can be obtained by combining the one or more active compounds with one or more solid excipients and, optionally, grinding the mixture.

Suitable auxiliaries may then be added and the mixture may be processed to form granules which may be used to form tablets or dragee cores. Other pharmaceutical solid preparations include push-fit capsules containing granules of one or more compound of the disclosure that can, in some embodiments, be mixed, for example, with fillers, binders, lubricants, stearate, stabilizers or combinations thereof. Push-fit capsules are well known and may be made of gelatin alone or gelatin in combination with one or more plasticizer such as glycerol or sorbitol to form a soft capsule. In embodiments in which soft capsules are utilized, compounds of the disclosure may be dissolved or suspended in one or more suitable liquids, such as, fatty oils or liquid paraffin and, in some cases, one or more stabilizers.

Liquid dosage formulations suitable for oral administration are also encompassed by embodiments of the disclosure. Such embodiments, may include one or more compounds of the disclosure in pharmaceutically acceptable emulsions, solutions, suspensions, syrups, and elixirs that may contain, for example, one or more inert diluents commonly used in the art such as, but not limited to, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (for example, cottonseed, groundnut, corn, germ, olive, castor, and sesame oils), glycerol, fatty acid derivatives of glycerol (for example, labrasol), tetrahydrofurfuryl alcohol, polyethylene glycols and fatty acid esters of sorbitan, and mixtures thereof. Suspensions may further contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Formulations for parenteral administration may include one or more compounds of the disclosure in water-soluble form, for example, water-soluble salts, alkaline solutions, and cyclodextrin inclusion complexes in a physiologically acceptable diluent which may be administered by injection. Physiologically acceptable diluent of such embodiments, may include, for example, sterile liquids such as water, saline, aqueous dextrose, other pharmaceutically acceptable sugar solutions; alcohols such as ethanol, isopropanol or hexadecyl alcohol; glycols such as propylene glycol or polyethylene glycol; glycerol ketals such as 2,2-dimethyl-1,3-dioxolane-4-methanol; ethers such as poly(ethyleneglycol) 400; pharmaceutically acceptable oils such as fatty acid, fatty acid ester or glyceride, or an acetylated fatty acid glyceride. In some embodiments, formulations suitable for parenteral administration may additionally include one or more pharmaceutically acceptable surfactants, such as a soap or detergent; suspending agent such as pectin, carbomers, methylcellulose, hydroxypropylmethylcellulose, or carboxymethylcellulose; an emulsifying agent; pharmaceutically acceptable adjuvants or combinations thereof. Additional pharmaceutically acceptable oils which may be useful in such formulations include those of petroleum, animal, vegetable or synthetic origin including, but not limited to, peanut oil, soybean oil, sesame oil, cottonseed oil, olive oil, sunflower oil, petrolatum, and mineral oil; fatty acids such as oleic acid, stearic acid, and isostearic acid; and fatty acid esters such as ethyl oleate and isopropyl myristate. Additional suitable detergents include, for example, fatty acid alkali metal, ammonium, and triethanolamine salts; cationic detergents such as dimethyl dialkyl ammonium halides, alkyl pyridinium halides, and alkylamine acetates; and anionic detergents, such as alkyl, aryl, and olefin sulfonates, alkyl, olefin, ether and monoglyceride sulfates, and sulfosuccinates. In some embodiments, non-ionic detergents including, but not limited to, fatty amine oxides, fatty acid alkanolamides and polyoxyethylenepolypropylene copolymers or amphoteric detergents such as alkyl-β-aminopropionates and 2-alkylimidazoline quaternary salts, and mixtures thereof may be useful in parenteral formulations of the disclosure.

In particular embodiments, alkaline salts such as ammonium salts of compounds of the disclosure may be prepared by the addition of, for example, Tris, choline hydroxide, Bis-Tris propane, N-methylglucamine, or arginine to a free base form of the compound. Such alkaline salts may be particularly well suited for use as parenterally administered forms of the compounds of the disclosure. Buffers, preservatives, surfactants and so on may also be added to formulations suitable for parenteral administration. For example, suitable surfactants may include polyethylene sorbitan fatty acid esters, such as sorbitan monooleate, and the high molecular weight adducts of ethylene oxide with a hydrophobic base, formed by the condensation of propylene oxide with propylene glycol.

Pharmaceutical compositions for parenteral administration may contain from about 0.5 to about 25% by weight of one or more of the compounds of the disclosure and from about 0.05% to about 5% suspending agent in an isotonic medium. In various embodiments, the injectable solution should be sterile and should be fluid to the extent that it can be easily loaded into a syringe. In addition, injectable pharmaceutical compositions may be stable under the conditions of manufacture and storage and may be preserved against the contaminating action of microorganisms such as bacteria and fungi.

Topical administration includes administration to the skin or mucosa, including surfaces of the lung and eye. Compositions for topical administration, may be prepared as a dry powder which may be pressurized or non-pressurized. In non-pressurized powder compositions, the active ingredients in admixture are prepared as a finely divided powder. In such embodiments, at least 95% by weight of the particles of the admixture may have an effective particle size in the range of 0.01 to 10 micrometers. In some embodiments, the finely divided admixture powder may be additionally mixed with an inert carrier such as a sugar having a larger particle size, for example, of up to 100 micrometers in diameter. Alternatively, the composition may be pressurized using a compressed gas, such as nitrogen or a liquefied gas propellant. In embodiments, in which a liquefied propellant medium is used, the propellant may be chosen such that the compound and/or an admixture including the compound do not dissolve in the propellant to any substantial extent. In some embodiments, a pressurized form of the composition may also contain a surface-active agent. The surface-active agent may be a liquid or solid non-ionic surface-active agent or may be a solid anionic surface-active agent, which in certain embodiments, may be in the form of a sodium salt.

Compositions for rectal administration may be prepared by mixing the compounds or compositions of the disclosure with suitable non-irritating excipients or carriers such as for example, cocoa butter, polyethylene glycol or a suppository wax. Such carriers may be solid at room temperature but liquid at body temperature and therefore melt in the rectum and release the drugs.

In still other embodiments, the compounds or compositions of the disclosure can be administered in the form of liposomes. Liposomes are generally derived from phospholipids or other lipid substances that form mono- or multilamellar hydrated liquid crystals when dispersed in an aqueous medium. Any non-toxic, physiologically acceptable and metabolizable lipid capable of forming liposomes can be used, and in particular embodiments, the lipids utilized may be natural and/or synthetic phospholipids and phosphatidyl cholines (lecithins). Methods to form liposomes are known in the art (see, for example, Prescott, Ed., Meth. Cell Biol. 14:33 (1976), which is hereby incorporated by reference in its entirety). Compositions including one or more compounds of the disclosure in liposome form can contain, for example, stabilizers, preservatives, excipients and the like.

In general, methods of embodiments of the disclosure may include the step of administering or providing an "effective amount" or a "therapeutically effective amount" of a compound or composition of the disclosure to an individual. In such embodiments, an effective amount of the compounds of the disclosure may be any amount that produces the desired effect. As described above, this amount may vary depending on, for example, the circumstances under which the compound or composition is administered (e.g., to incite treatment or prophylactically), the type of individual, the size, health, etc. of the individual and so on. The dosage may further vary based on the severity of the condition. For example, a higher dose may be administered to treat an individual with a well-developed metastatic condition, compared to the amount used to prevent a subject from developing the metastatic condition. Those skilled in the art can discern the proper dosage based on such factors. For example, in some embodiments, the dosage may be within the range of about 0.01 mg/kg body weight to about 300 mg/kg body weight or between about 0.1 mg/kg body weight and about 100 mg/kg body weight, and in particular embodiments, the dosage may be from about 0.1 mg/kg body weight to about 10 mg/kg body weight.

The administration schedule may also vary. For example, in some embodiments, the compounds or compositions of the disclosure may be administered in a single dose once per day or once per week. In other embodiments, the compounds or compositions of the disclosure may be administered in two, three, four or more doses per day or per week. For example, in one embodiment, an effective amount for a single day may be divided into separate dosages that may contain the same or a different amount of the compound or composition and may be administered several times throughout a single day. Without wishing to be bound by theory, the dosage per administration and frequency of administration may depend, for example, on the specific compound or composition used, the condition being treated, the severity of the condition being treated, and the age, weight, and general physical condition of the individual to which the compound or composition is administered and other medications which the individual may be taking. In another exemplary embodiment, treatment may be initiated with smaller dosages that are less than the optimum dose of the compound, and the dosage may be increased incrementally until a more optimum dosage is achieved.

In each of the embodiments above, the compound administered can be provided as a pharmaceutical composition including compound as described above and a pharmaceutically acceptable excipient or a pure form of the compound may be administered.

In additional embodiments, the compound or composition of the disclosure may be used alone or in combination with one or more additional agents. For example, in some embodiments, a compound or composition of disclosure may be formulated with one or more additional anti-cancer agents or combinations thereof such that the pharmaceutical composition obtained including the compound or composition of the disclosure and the one or more additional agents can be delivered to an individual in a single dose. In other embodiments, the compound or composition of the disclosure may be formulated as a separate pharmaceutical composition that is delivered in a separate dose from pharmaceutical compositions including the one or more additional agents. In such embodiments, two or more pharmaceutical compositions may be administered to deliver effective amounts of a compound or composition of the disclosure and the one or more additional agents. For example, in some embodiments, one or more compounds of formulae I-VI may be administered in combination with or co-administered with doxorubicin, paclitaxel, methotrexate, tamoxifen, cyclophosphamide, vincristine, etoposide, streptozotocin and 5-fluorouracil, and in particular embodiments, one or more of the compounds of the disclosure may be administered with paclitaxel.

Other changes may be made without departing from the spirit and scope of the disclosure.

The invention claimed is:

1. A method for inhibiting metastases in an individual afflicted with prostate cancer comprising administering to the individual a therapeutically effective amount of a compound that binds to a PH domain of a Tiam-1 protein and which disrupts Tiam-1 activity, wherein the compound is of Formula IIA or Formula IIB, (IIA)

(IIB)

where $R_4$ is selected from —H, —CH$_3$, and —CH$_2$CH$_3$;
$R_7$ is selected from —H and a five or six member ring selected from , , , and ;

$R_6$ is selected from —SCH$_2$—, —COCH$_2$—, —CONH—, and —CH$_2$CH$_2$—;
$R_7$ is selected from the group consisting of —H, =O, =S; and $R_8$ is selected from the group consisting of —CH$_3$, —CH$_2$CH$_2$NH$_2$, —CH$_2$—C$_6$H$_5$, CH$_2$COOH, , and .

2. The method of claim 1, wherein the compound is selected from one or more of Formula V, (V)

Formula VII, (VII)

Formula VIII,
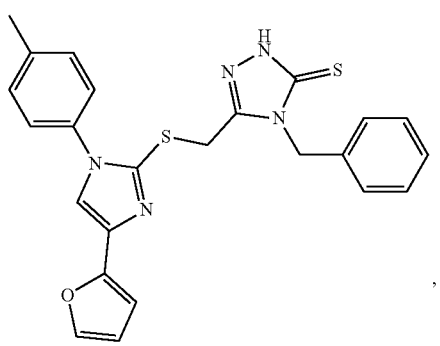
Formula IX,
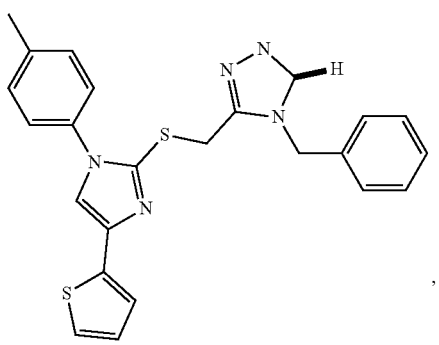
Formula X,
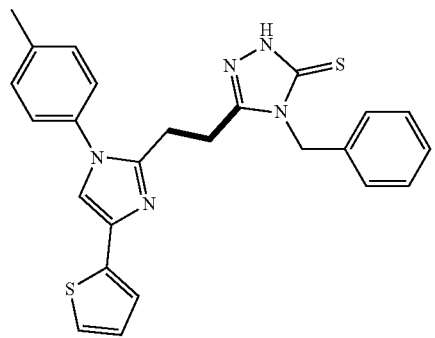
Formula XI,
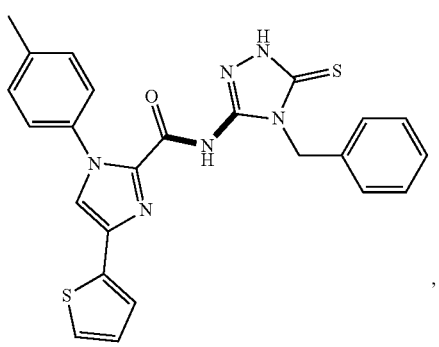
Formula XII,
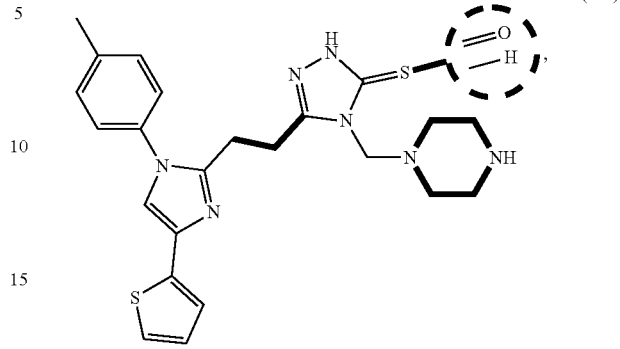
—CO—NH—
—S—CH$_2$—
Formula XIII,
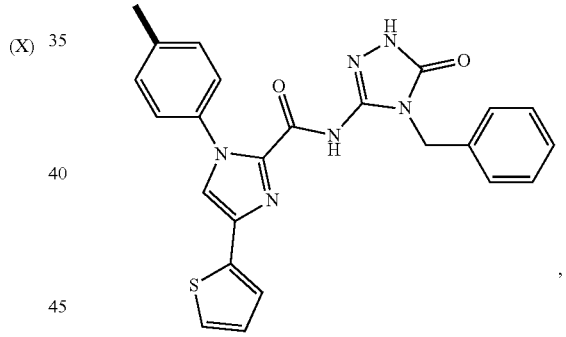
Formula XIV,
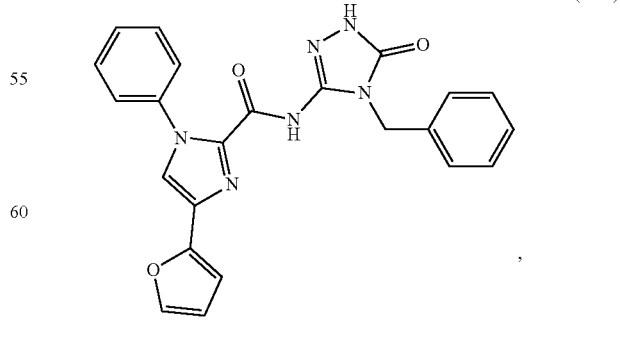

Formula XV,
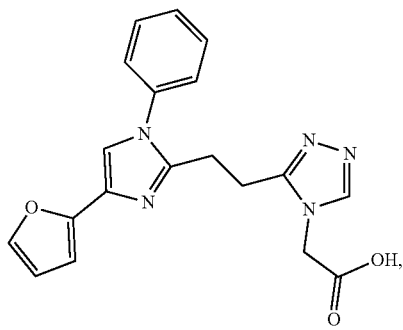
Formula XVI,
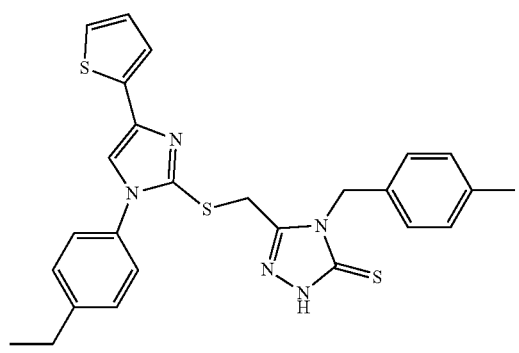
Formula XVII,
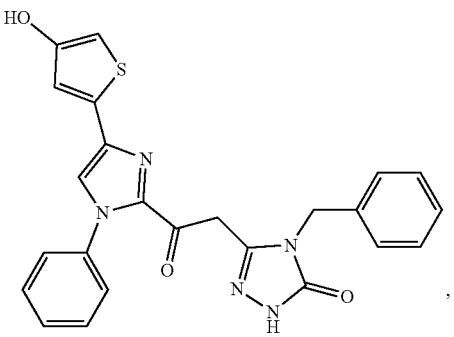
Formula XVIII,
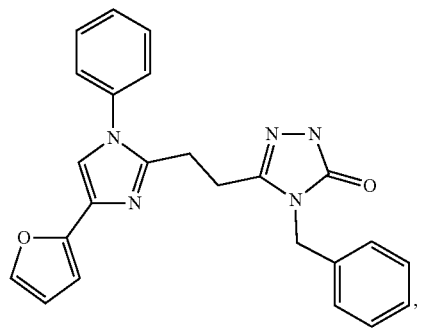
Formula XIX,
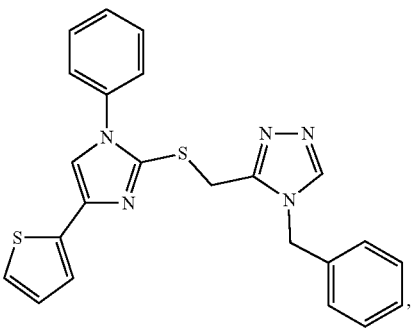
Formula XX,
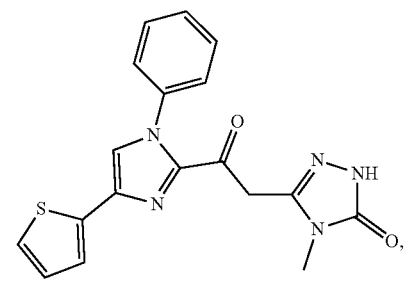
Formula XXI,
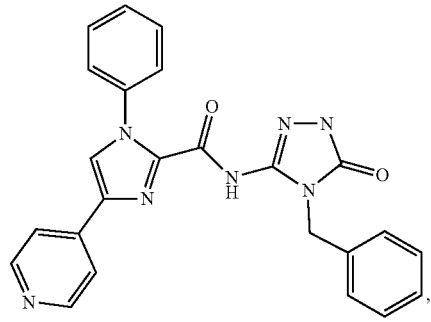
Formula XXII,
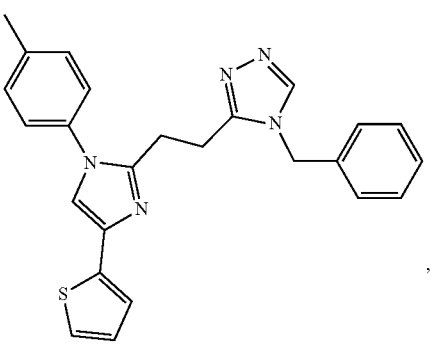

and pharmaceutically acceptable salts of any of Formula V, and Formula VII through Formula XXII.

3. The method according to claim 1, wherein the therapeutically effective amount is in a range of 10 milligrams/day to 10,000 milligrams/day.

4. The method according to claim 1, wherein the individual is a mammal.

5. The method according to claim 2, wherein the therapeutically effective amount is in a range of 10 milligrams/day to 10,000 milligrams/day.

6. The method according to claim 2, wherein the individual is a mammal.

7. A method for inhibiting metastases in an individual afflicted with prostate cancer comprising administering to the individual a therapeutically effective amount of a compound that binds to a PH domain of a Tiam-1 protein and disrupts Tiam-1 activity, wherein the compound is of Formula III, (III)

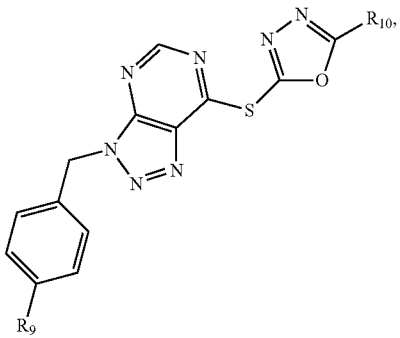

where $R_9$ is selected from the group consisting of —H, and —CH$_3$; and $R_{10}$ is

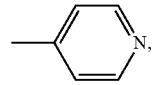

and pharmaceutically acceptable salts of Formula III.

8. The method according to claim 7, wherein the individual is a mammal and the therapeutically effective amount is in a range of 10 milligrams/day to 10,000 milligrams/day.

9. The method of claim 7, wherein the compound is of Formula VI, (VI)

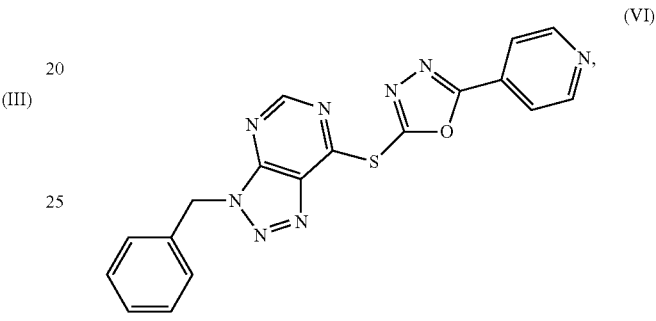

and pharmaceutically acceptable salts thereof.

10. The method according to claim 9, wherein the individual is a mammal and the therapeutically effective amount is in a range of 10 milligrams/day to 10,000 milligrams/day.

* * * * *